United States Patent
Zhong et al.

(10) Patent No.: US 9,657,351 B2
(45) Date of Patent: May 23, 2017

(54) MRNA-BASED GENE EXPRESSION FOR PERSONALIZING PATIENT CANCER THERAPY WITH AN MDM2 ANTAGONIST

(71) Applicant: Hoffmann-La Roche Inc., Nutley, NJ (US)

(72) Inventors: Hua Zhong, Short Hills, NJ (US); David Geho, Allendale, NJ (US); Gong Chen, Rutherford, NJ (US); Gwen Nichols, New York, NY (US); Markus Dangl, Seeshaupt (DE)

(73) Assignee: HOFFMAN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/560,519

(22) Filed: Dec. 4, 2014

(65) Prior Publication Data

US 2015/0211073 A1 Jul. 30, 2015

Related U.S. Application Data

(60) Provisional application No. 61/912,781, filed on Dec. 6, 2013.

(51) Int. Cl.
*A61K 31/40* (2006.01)
*C12Q 1/68* (2006.01)
*A61K 31/496* (2006.01)

(52) U.S. Cl.
CPC ............ *C12Q 1/6886* (2013.01); *A61K 31/40* (2013.01); *A61K 31/496* (2013.01); *C12Q 2600/106* (2013.01); *C12Q 2600/158* (2013.01); *C12Q 2600/16* (2013.01)

(58) Field of Classification Search
CPC .............................. A61K 31/40; A61K 31/496
USPC ........................................................ 514/408
See application file for complete search history.

(56) References Cited

U.S. PATENT DOCUMENTS

2010/0152190 A1 6/2010 Bartkovitz et al.
2012/0046186 A1 2/2012 Pelham et al.

FOREIGN PATENT DOCUMENTS

WO 2004/111603 A2 12/2004
WO 2007063013 A1 6/2007
WO 2009/140304 A1 11/2009
WO 2013135648 A1 9/2013
WO 2014020502 A2 2/2014

OTHER PUBLICATIONS

B. Hu et al., "MDMX Overexpression Prevents p53 Activation by the MDM2 Inhibitor Nutlin" Journal of Biological Chemistry 281(44):33030-33035 (Sep. 6, 2006).
Drakos E. et al., "Activation of the p53 pathway by the MDM2 inhibitor nutlin-3a overcomes BCL2 overexpression in a preclinical model of diffuse large B-cell lymphoma associated with t(14;18)(q32;q21)" Leukemia 25(5):856-867 (Mar. 11, 2011).
Chris Saddler et al., "Comprehensive biomarker and genomic analysis identifies p53 status as the major determinant of response to MDM2 inhibitors in chronic lymphocytic leukemia" Blood 111(3):1584-1593 (Oct. 25, 2007).
Stanislaw Krajewski, et al., "Reduced Expression of Proapoptotic Gene BAX is Associated with Poor Response Rates to Combination Chemotherapy and Shorter Survival in Women with Metastatic Breast Adenocarcinoma" Cancer Research 55(19):4471-4478 (Oct. 1, 1995).
Binh Vu et al., "Discovery of RG7112: A Small-Molecule MDM2 Inhibitor in Clinical Development" ACS Medicinal Chemistry Letters 4(5):466-469 (May 9, 2013).
Sanjeev Shangary et al., "Small-Molecule Inhibitors of the MDM-p53 Protein-Protein Interaction to Reactive p53 Function: A Novel Approach for Cancer Therapy" Annual Review of Pharmacology and Toxicology 49(1):223-241 (Feb. 1, 2009).
Hege O. Ohnstad et al., "Correlation of TP53 and MDM2 Genotypes With Response to Therapy in Sarcoma" Cancer 119(5):1013-1022 (Nov. 16, 2012).
Kensuke Kojima et al., "Mdm2 inhibitor Nutlin-3a induces p53-mediated apoptosis by transcription-dependent and transcription-independent mechanisms and may overcome Atm-mediated resistance to fludarabine in chronic lymphocytic leukemia" Blood 108(3):993-1000 (Aug. 1, 2006).
Patton J.T, "Levels of HdmX Expression Dictate the Sensitivity of Normal and Transformed Cells to Nutlin-3" Cancer Research 66(6):3169-3176 (Mar 15, 2006).
Christoph R. Mueller et al., "Potential for treatment of liposarcomas with the MDM2 antagonist Nutlin-3A" International Journal of Cancer 121(1):199-205 (Jul. 1, 2007).
The International Search Report and Written Opinion, mailed on Dec. 22, 2014, in the related PCT Appl. No. PCT/EP14/64039.
The Singapore Search Report and Written Opinion, issued on Nov. 29, 2016, in the related Singapore patent application No. 11201510816S.
Saha et al., "MDM2 antagonist nutlin plus proteasome inhibitor velcade combination displays a synergistic anti-myeloma activity," Cancer Biol Ther. Jun. 1, 2010; 9(11):936-44.

*Primary Examiner* — Raymond Henley, III

(57) ABSTRACT

Use of at least an MDM2 gene panel, preferably a four gene MDM2 gene panel, as a biomarker for predicting the response to a MDM2 antagonist.

16 Claims, 5 Drawing Sheets

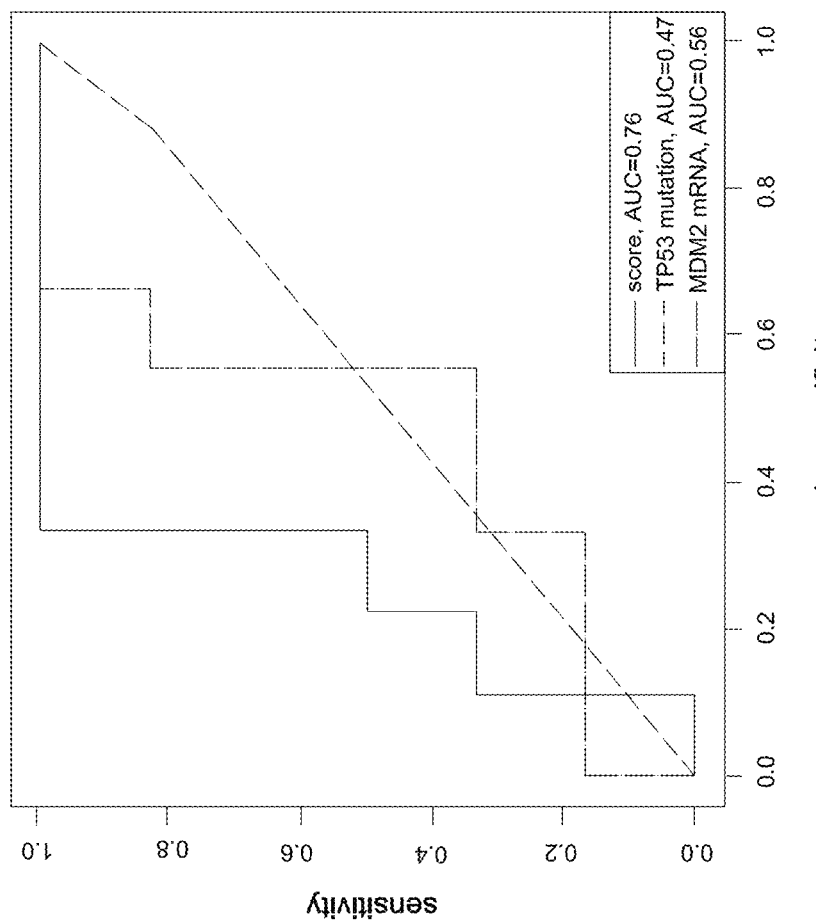
FIG. 4B (high exposure)

MRNA-BASED GENE EXPRESSION FOR PERSONALIZING PATIENT CANCER THERAPY WITH AN MDM2 ANTAGONIST

This application claims the benefit of U.S. Provisional Application No. 61/912,781, filed Dec. 6, 2013. The entire contents of the above-identified application is hereby incorporated by reference.

BACKGROUND OF THE INVENTION

The TP53 gene encodes a tumor suppressor protein that plays a critical role in the protection during the development of cancers. P53 is crucial in multi-cellular organisms where it regulates cell cycle, and thus acts as a tumor suppressor that is involved in preventing cancer. Further, it is a transcription factor that regulates multiple genes involved in cell cycle control, such as apoptosis, DNA repair and senescence.

Under non-stressed conditions, the level of p53 protein is controlled by MDM2 (Murine Double Minute 2) via a negative feedback loop, wherein MDM2 transcription is driven by p53. MDM2 protein binds to the TP53 protein and blocks its transactivation domain. MDM2 can also function as a p53 ubiquitin ligase, which marks p53 for ubiquitin dependent degradation.

In cells that overexpress MDM2, P53 is inactivated, leading to inefficient growth arrest and apoptosis. Blocking the P53-MDM2 interaction might restore P53 function and could be a novel approach to cancer treatment. Treatment of tumor cells with MDM2 antagonists should enable p53 to mediate its downstream functions, including activation of gene transcription and induction of cell cycle arrest and apoptosis.

TP53 mutations are rare in Acute Myeloid Leukemia (AML) and are generally not considered to be of primary importance in the development of these malignancies. However, MDM2 has been found to be frequently overexpressed in AML, and can enhance the tumorigenic potential and resistance to apoptosis through abrogation of p53 function. It has been found that AML cell lines and 16 primary aAML samples with wild-type p53 responded to MDM2 antagonist (inhibitor) by induction of p53-dependent apoptosis. These findings support the rationale of targeting the p53-MDM2 interaction as a therapeutic strategy for AML.

Based on the proposed mechanism of action of the drug, the presence of functional p53 protein and related pathway effector molecules are required for this class of drugs to be efficacious. Not all patients will have functional p53 proteins and related pathway effector molecules. In order to better determine whether a patient can benefit from therapy, there is a need to discover predictive molecular tests for identifying patients that are most likely to respond to therapy. One approach for assessing potential response to a MDM2 antagonist is to assess whether or not the TP53 gene is mutated. However, this is complicated by the fact that a multitude of mutations can be found in TP53 in cancer. Not all of these mutations will interfere with activity of the p53 protein, further complicating interpretation of TP53 mutational tests. In addition, there is a range of responses to MDM2 antagonists in wild type TP53 cell lines and patients. Therefore, the ability to predict responsiveness to an MDM2 antagonist from an easily interpretable diagnostic tool is an unmet need in clinical development of MDM2 antagonists. To this end, the development of a gene expression signature that reflects p53 pathway activity could provide a means of selecting patients most likely to respond to MDM2 antagonist therapy.

SUMMARY OF THE INVENTION

An aspect of the present invention relates to a method for predicting the response of a disease in a (subject) patient to a cancer disease, wherein the patients therapy is treatment to a compound of formula I or formula II or formula III or combinations thereof, and general pharmaceutically acceptable derivatives thereof as defined, said method comprising the steps of:
  a) measuring a level in a sample pre-obtained from the subject to obtain a value or values representing this level; and
  b) comparing the value or values from step a) to a standard value or set of standard values.

The compounds of formula I are disclosed in U.S. Pat. No. 8,354,444 B2, incorporated in its entirety herein. Compounds of formula I are also published in WO2011/098398. "Compound A" as used herein (sometimes also referred to as RG7112) is disclosed in WO 2007/063013. Below is provided the compounds useful in the present invention.

Compounds of the formula I are useful in the present invention and are defined below:

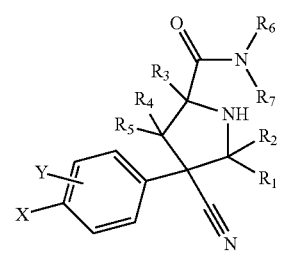

wherein
X is selected from the group consisting of H, F, Cl, Br, I, cyano, nitro, ethynyl, cyclopropyl, methyl, ethyl, isopropyl, vinyl and methoxy,
Y is one to four group(s) independently selected from the group consisting of H, F, Cl, Br, I, CN, OH, nitro, lower alkyl, cycloalkyl, lower alkoxy, lower alkenyl, cycloalkenyl, lower alkynyl, aryl, hetereoaryl, hetereocycle, COOR', OCOR', CONR'R", NR'COR", NR"SO$_2$R', SO$_2$NR'R" and NR'R" wherein
R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, hetereoaryl, substituted hetereoaryl, hetereocycle, or substituted hetereocycle.
and in the case of R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle,
one of R$_1$ and R$_2$ is selected from the group consisting of lower alkyl,
substituted lower alkyl, lower alkenyl, substituted lower alkenyl, aryl, substituted aryl, heteroaryl, substituted hetereoaryl, heterocycle, substituted heterocycle, cycloalkyl, substituted cycloalkyl, cycloalkenyl, and substituted cycloalkenyl and the other is hydrogen or lower alkyl, $R_3$ is H or lower alkyl, one of $R_4$ and $R_5$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, $R_6$ and $R_7$ are selected from the group consisting of $(CH_2)_n$—R', $(CH_2)_n$—NR'R", $(CH_2)_n$—NR'COR", $(CH_2)_n$—NR'SO$_2$R", $(CH_2)_n$—COOH, $(CH_2)_n$—COOR', $(CH_2)_n$—CONR'R", $(CH_2)_n$—OR', $(CH_2)_n$—SR', $(CH_2)_n$—SOR', $(CH_2)_n$—SO$_2$R', $(CH_2)_n$—COR', $(CH_2)_n$—SO$_3$H, $(CH_2)_n$—SONR"R", $(CH_2)_n$—SO$_2$NR'R", $(CH_2CH_2O)_m$—$(CH_2)_n$—R', $(CH_2CH_2O)_m$—$(CH_2)_n$—OH, $(CH_2CH_2O)_m$—$(CH_2)_n$—OR', $(CH_2CH_2O)_m$—$(CH_2)_n$—NR'R", $(CH_2CH_2O)_m$—$(CH_2)_n$—NR'COR", $(CH_2CH_2O)_m$—$(CH_2)_n$—NR'SO$_2$R", $(CH_2CH_2O)_m$—$(CH_2)_n$—COOH, $(CH_2CH_2O)_m$—$(CH_2)_n$—COOR', $(CH_2CH_2O)_m$—$(CH_2)_n$—CONR'R", $(CH_2CH_2O)_m$—$(CH_2)_n$—SO$_2$R', $(CH_2CH_2O)_m$—$(CH_2)_n$—COR', $(CH_2CH_2O)_m$—$(CH_2)_n$—SONR'R", $(CH_2CH_2O)_m(CH_2)_n$—SO$_2$NR'R", $(CH_2)_p$—$(CH_2CH_2O)_m$—$(CH_2)_n$—R', $(CH_2)_p$—$(CH_2CH_2O)_m$—$(CH_2)_n$—OH, $(CH_2)_p$—$(CH_2CH_2O)_m$—$(CH_2)_n$—OR', $(CH_2)_p$—$(CH_2CH_2)_m$—$(CH_2)_n$—NR'R", $(CH_2)_p$—$(CH_2CH_2O)_m$—$(CH_2)_n$—NR'COR", $(CH_2)_p$—$(CH_2CH_2O)_m$—$(CH_2)_n$—NR'SO$_2$R", $(CH_2)_p$—$(CH_2CH_2O)_m$—$(CH_2)_n$—COOH, $(CH_2)_p$—$(CH_2CH_2O)_m$—$(CH_2)_n$—COOR', $(CH_2)_p$—$(CH_2CH_2O)_m$—$(CH_2)_n$—CONR'R", $(CH_2)_p$—$(CH_2CH_2O)_m$—$(CH_2)_n$—SO$_2$R', $(CH_2)_p$—$(CH_2CH_2O)_m$—$(CH_2)_n$—COR', $(CH_2)_p$—$(CH_2CH_2O)_m$—$(CH_2)_n$—SONR'R", $(CH_2)_p$—$(CH_2CH_2O)_m$—$(CH_2)_n$—SO$_2$NR'R", —SOR' and SO$_2$R' wherein R' and R" are as above, m, n and p are independently 0 to 6 and the pharmaceutically acceptable salts and esters thereof.

Preferred are compounds of formula I having a stereochemical structure as shown as formula II

II wherein

X is selected from the group consisting of H, F, Cl, Br, I, cyano, nitro, ethynyl, cyclopropyl, methyl, ethyl, isopropyl, vinyl and methoxy, Y is one to four group(s) independently selected from the group consisting of H, F, Cl, Br, I, CN, OH, nitro, lower alkyl, cycloalkyl, lower alkoxy, lower alkenyl, cycloalkenyl, lower alkynyl, aryl, hetereoaryl, hetereocycle, COOR', OCOR', CONR'R", NR"COR", NR"SO$_2$R', SO$_2$NR'R" and NR'R" wherein R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, hetereocycle, or substituted hetereocycle, and wherein R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle, $R_1$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl, $R_2$ is hydrogen or lower alkyl, $R_3$ is H or lower alkyl, $R_5$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl, $R_4$ is hydrogen, $R_6$ and $R_7$ are selected from the group consisting of $(CH_2)_n$—R', $(CH_2)_n$—NR'R", $(CH_2)_n$—NR'COR", $(CH_2)_n$—NR'SO$_2$R", $(CH_2)_n$—COOH, $(CH_2)_n$—COOR', $(CH_2)_n$—CONR'R", $(CH_2)_n$—OR', $(CH_2)_n$—SR', $(CH_2)_n$—SOR', $(CH_2)_n$—SO$_2$R', $(CH_2)_n$—COR', $(CH_2)_n$—SO$_3$H, $(CH_2)_n$—SONR'R", $(CH_2)_n$—SO$_2$NR'R", $(CH_2CH_2O)_m$—$(CH_2)_n$—R', $(CH_2CH_2O)_m$—$(CH_2)_n$—OH, $(CH_2CH_2O)_m$—$(CH_2)_n$—OR', $(CH_2CH_2O)_m$—$(CH_2)_n$—NR'R", $(CH_2CH_2O)_m$—$(CH_2)_n$—NR'COR", $(CH_2CH_2O)_m$—$(CH_2)_n$—NR'SO$_2$R", $(CH_2CH_2O)_m$—$(CH_2)_n$—COOH, $(CH_2CH_2O)_m$—$(CH_2)_n$—COOR', $(CH_2CH_2O)_m$—$(CH_2)_n$—CONR'R", $(CH_2CH_2O)_m$—$(CH_2)_n$—SO$_2$R', $(CH_2CH_2O)_m$—$(CH_2)_n$—COR', $(CH_2CH_2O)_m(CH_2)_n$—SONR'R", $(CH_2CH_2O)_m$—$(CH_2)_n$—SO$_2$NR'R", $(CH_2)_p$—$(CH_2CH_2O)_m(CH_2)_n$—R', $(CH_2)_p$—$(CH_2CH_2O)_m(CH_2)_n$—OH, $(CH_2)_p$—$(CH_2CH_2O)_m$—$(CH_2)_n$—OR', $(CH_2)_p$—$(CH_2CH_2O)_m$—$(CH_2)_n$—NR'R", $(CH_2)_p$—$(CH_2CH_2O)_m$—$(CH_2)_n$—NR'COR", $(CH_2)_p$—$(CH_2CH_2O)_m$—$(CH_2)_n$—NR'SO$_2$R", $(CH_2)_p$—$(CH_2CH_2O)_m(CH_2)_n$—COOH, $(CH_2)_p$—$(CH_2CH_2O)_m$—$(CH_2)_n$—COOR', $(CH_2)_p$—$(CH_2CH_2O)_m(CH_2)_n$—CONR'R", $(CH_2)_p$—$(CH_2CH_2O)_m$—$(CH_2)_n$—SO$_2$R', $(CH_2)_p$—$(CH_2CH_2O)_m$—$(CH_2)_n$—COR', $(CH_2)_p$—$(CH_2CH_2O)_m$—$(CH_2)_n$—SONR'R", $(CH_2)_p$—$(CH_2CH_2O)_m$—$(CH_2)_n$—SO$_2$NR'R", —COR', —SOR' and SO$_2$R' wherein R' and R" are as above, m, n, and p are independently 0 to 6 and the pharmaceutically acceptable salts and esters thereof.

Especially preferred are compounds of formula II wherein X is F, Cl or Br,

Y is one to two group(s) independently selected from the group consisting of H, F, Cl, Br, I, CN, OH, nitro, lower alkyl, cycloalkyl, lower alkoxy, lower alkenyl, lower cycloalkenyl and lower alkynyl, $R_1$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl, $R_2$ is hydrogen, $R_3$ is H, $R_5$ is selected from the group consisting of aryl, substituted aryl, heteroaryl and substituted heteroaryl, $R_4$ is hydrogen, $R_6$ and $R_7$ are selected from the group consisting of $(CH_2)_n$—R', $(CH_2)_n$—NR'R", $(CH_2)_n$—NR'COR", $(CH_2)_n$—NR'SO$_2$R", $(CH_2)_n$—COOH, $(CH_2)_n$—COOR', $(CH_2)_n$—CONR'R", $(CH_2)_n$—OR', $(CH_2)_n$—SR', $(CH_2)_n$—SOW, $(CH_2)_n$—SO$_2$R', $(CH_2)_n$—COR', $(CH_2)_n$—SO$_3$H, $(CH_2)_n$—SONR'R", $(CH_2)_n$—SO$_2$NR'R", $(CH_2CH_2O)_m$—$(CH_2)_n$—R', $(CH_2CH_2O)_m$—$(CH_2)_n$—OH, $(CH_2CH_2O)_m$—$(CH_2)_n$—OR', $(CH_2CH_2O)_m$—$(CH_2)_n$—NR'R", $(CH_2CH_2O)_m$—$(CH_2)_n$—NR'COR", $(CH_2CH_2O)_m$—$(CH_2)_n$—NR'SO$_2$R", $(CH_2CH_2O)_m$—$(CH_2)_n$—COOH, $(CH_2CH_2O)_m$—$(CH_2)_n$—COOR', $(CH_2CH_2O)_m$—$(CH_2)_n$—CONR'R", $(CH_2CH_2O)_m$—$(CH_2)_n$—SO$_2$R', $(CH_2CH_2O)_m$—$(CH_2)_n$—COR', $(CH_2CH_2O)_m$—$(CH_2)_n$—SONR'R", $(CH_2CH_2O)_m$—$(CH_2)_n$—SO$_2$NR'R", $(CH_2)_p$—$(CH_2CH_2O)_m$—$(CH_2)_n$—R', $(CH_2)_p$—$(CH_2CH_2O)_m$—$(CH_2)_n$—OH, $(CH_2)_p$—$(CH_2CH_2O)_m$—$(CH_2)_n$—OR', $(CH_2)_p$—$(CH_2CH_2O)_m$—$(CH_2)_n$—NR'R", $(CH_2)_p$—$(CH_2CH_2O)_m$—$(CH_2)_n$—NR'COR", $(CH_2)_p$—$(CH_2CH_2O)_m$—$(CH_2)_n$—NR'SO$_2$R", $(CH_2)_p$—$(CH_2CH_2O)_m$—$(CH_2)_n$—COOH, $(CH_2)_p$—$(CH_2CH_2O)_m$—$(CH_2)_n$—COOR', $(CH_2)_p$—$(CH_2CH_2O)_m$—$(CH_2)_n$—CONR'R", $(CH_2)_p$—$(CH_2CH_2O)_m$—$(CH_2)_n$—SO$_2$R', $(CH_2)_p$—$(CH_2CH_2O)_m$—$(CH_2)_n$—COR', $(CH_2)_p$—$(CH_2CH_2O)_m$—$(CH_2)_n$—SONR'R", $(CH_2)_p$—$(CH_2CH_2O)_m$—$(CH_2)_n$—SO$_2$NR'R", —COR', —SOW and SO$_2$R' wherein R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, hetereocycle, or substituted hetereocycle, and wherein R' and R" may also independently link to form a cyclic structure selected from substituted or unsubstituted cycloalkyl, substituted or unsubstituted cycloalkenyl, substituted or unsubstituted heteroaryl or substituted or unsubstituted heterocycle, m, n and p are independently 0 to 6 and the pharmaceutically acceptable salts and esters thereof.

Further preferred are compounds of formula II wherein:
X is F, Cl or Br,
Y is a mono-substituting group selected from H or F and
$R_1$ is selected from the group consisting of lower alkyl, substituted lower alkyl, lower alkenyl, substituted lower alkenyl, heterocycle, substituted heterocycle, cycloalkyl, substituted cycloalkyl, cycloalkenyl and substituted cycloalkenyl.

Further preferred $R_1$ is a substituted lower alkyl selected from:

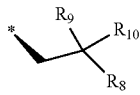

where $R_8$, $R_9$ are both methyl, or linked to form a cyclopropyl, cyclobutyl, cyclopentyl or acyclohexyl group,
$R_{10}$ is $(CH_2)_m$—$R_{11}$,
m is 0, 1 or 2,
$R_{11}$ is selected from hydrogen, hydroxyl, lower alkyl, lower alkoxy, aryl, substituted aryl. heteroaryl, substituted heteroaryl, hetereocycle or substituted heterocycle,
$R_2$ is H,
$R_3$ is H,
$R_5$ is a substituted phenyl selected from:

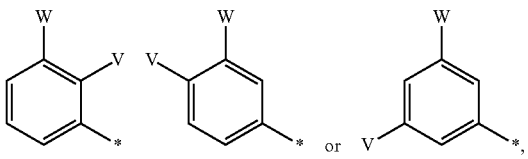

W is F, Cl or Br,
V is H or F,
$R_4$ is hydrogen,
one of $R_6$ and $R_7$ is hydrogen and the other is $(CH_2)_n$—R',
n is 0 or 1 and
R' is selected from aryl, substituted aryl, hetereoaryl, substituted heteroaryl, hetereocycle or substituted heterocycle.

In yet another embodiment, the present invention is directed to the use of compounds of formula IIa

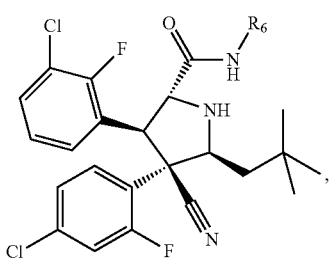

(IIa)

wherein $R_6$ and all variables and substituents mentioned in the definitions for $R_6$ have the meanings given for formula II above.

In still another embodiment, there are provided the compounds of formula IIa used in the present invention, wherein
$R_6$ is —$(CH_2)_n$—R', and
R' is Cyclohexyl, or
a 5 to 10 membered, mono- or bicyclic aromatic hydrocarbon wherein 1 or 2 carbon atoms may be replaced by N, S or O, and wherein any of the aforementioned cyclohexyl or aromatic hydrocarbon can be substituted once or twice with a group independently selected from lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsufonyl, amino-sulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$; and
n is 0 or 1.

In still another preferred embodiment there are provided the compounds of formula IIa used in the present invention, wherein R6 is —(CH$_2$)$_n$—R', and R' is phenyl, pyridinyl, pyrazinyl or pyrimidinyl which can be each unsubstituted or once or twice substituted with a substituent independently selected from halogen, C1-6 alkoxy, C1-6 alkyl, hydroxycarbonyl, carboxy, carboxy C1-6 alkoxy, oxo and CN; and n is 0.

Especially preferred are the compounds of formula IIa to be used in the present invention, selected from rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-cyclohexanecarboxylic acid methyl ester, rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-cyclohexanecarboxylic acid, rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid methyl ester, rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid, rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-fluoro-benzoic acid methyl ester, rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-fluoro-benzoic acid, chiral 5-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-pyridine-2-carboxylic acid methyl ester, chiral 5-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-pyridine-2-carboxylic acid, chiral 6-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-nicotinic acid ethyl ester, chiral 6-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-nicotinic acid, rac 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-ethoxy-benzoic acid, chiral (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-hydrazinocarbonyl-phenyl)-amide, chiral [2-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-ethyl]-carbamic acid tert-butyl ester, chiral (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-amino-ethyl)-phenyl]-amide, chiral 5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-pyrazine-2-carboxylic acid, chiral 4-(((2R,3S,4R,5S)-3-(3-chloro-2-fluorophenyl)-4-(4-chloro-2-fluorophenyl)-4-cyano-5-neopentylpyrrolidine-2-carboxamido)methyl)-2-methoxybenzoic acid, chiral-4-({[(2S,3R,4S,5R)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid, chiral methyl 3-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)propanoate, chiral 3-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)propanoic acid, chiral-4-(((2S,3R,4S,5R)-3-(3-chloro-2-fluorophenyl)-4-(4-chloro-2-fluorophenyl)-4-cyano-5-neopentylpyrrolidine-2-carboxamido)methyl)-2-fluorobenzoic acid, chiral 4-(((2R,3S,4R,5S)-3-(3-chloro-2-fluorophenyl)-4-(4-chloro-2-fluorophenyl)-4-cyano-5-neopentylpyrrolidine-2-carboxamido)methyl)-2-fluorobenzoic acid, chiral (2R,3S,4R,5S)-3-(3-chloro-2-fluorophenyl)-4-(4-chloro-2-fluorophenyl)-4-cyano-N-(2-morpholinopyrimidin-5-yl)-5-neopentylpyrrolidine-2-carboxamide, chiral (2R,3S,4R,5S)-3-(3-chloro-2-fluorophenyl)-4-(4-chloro-2-fluorophenyl)-4-cyano-5-neopentyl-N-(pyrimidin-5-yl)pyrrolidine-2-carboxamide, chiral (2S,3R,4S,5R)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide, chiral methyl 5-((2R,3S,4R,5S)-3-(3-chloro-2-fluorophenyl)-4-(4-chloro-2-fluorophenyl)-4-cyano-5-neopentylpyrrolidine-2-carboxamido)-1H-benzo[d]imidazole-2-carboxylate, chiral-5-((2R,3S,4R,5S)-3-(3-chloro-2-fluorophenyl)-4-(4-chloro-2-fluorophenyl)-4-cyano-5-neopentylpyrrolidine-2-carboxamido)-1H-benzo[d]imidazole-2-carboxylic acid, chiral-methyl 5-((2R,3S,4R,5S)-3-(3-chloro-2-fluorophenyl)-4-(4-chloro-2-fluorophenyl)-4-cyano-5-neopentylpyrrolidine-2-carboxamido)benzofuran-2-carboxylate, chiral-5-((2R,3S,4R,5S)-3-(3-chloro-2-fluorophenyl)-4-(4-chloro-2-fluorophenyl)-4-cyano-5-neopentylpyrrolidine-2-carboxamido)benzofuran-2-carboxylic acid, chiral-methyl 4-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)butanoate, chiral-4-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)butanoic acid, chiral methyl 5-((2R,3S,4R,5S)-3-(3-chloro-2-fluorophenyl)-4-(4-chloro-2-fluorophenyl)-4-cyano-5-neopentylpyrrolidine-2-carboxamido)benzo[d]oxazole-2-carboxylate, chiral-5-((2R,3S,4R,5S)-3-(3-chloro-2-fluorophenyl)-4-(4-chloro-2-fluorophenyl)-4-cyano-5-neopentylpyrrolidine-2-carboxamido)benzo[d]oxazole-2-carboxylic acid, chiral-(2R,3S,4R,5S)—N-(benzo[d]oxazol-5-yl)-3-(3-chloro-2-fluorophenyl)-4-(4-chloro-2-fluorophenyl)-4-cyano-5-neopentylpyrrolidine-2-carboxamide, rac-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-benzyl)-carbamic acid tert-butyl ester, rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-aminomethyl-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(methanesulfonylaminomethyl)-phenyl]-amide, 1-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-piperidine-4-carboxylic acid ethyl ester, 1-(4-{[(2R,3S,4R,5 S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-piperidine-4-carboxylic acid, rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide, rac-5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-pyrrolidin-1-yl-benzoic acid, rac-4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-4-methyl-piperidine-1-carboxylic acid tert-butyl ester, rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-methyl-piperidin-4-yl)-amide, rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (1-methanesulfonyl-4-methyl-piperidin-4-yl)-amide, methyl 1-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)pyrrolidine-2-carboxylate, 1-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)pyrrolidine-2-carboxylic acid, chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-pyrrole-2-carboxylic acid, chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-pyrrole-2-carboxylic acid ethyl ester, chiral (R)-2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid, chiral (S)-2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid, chiral (S)-2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid methyl ester, chiral (S)-2-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid methyl ester, chiral (S)-2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid, chiral (S)-2-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid, chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-indole-2-carboxylic acid, rac (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (5-iodo-pyridin-2-yl)-amide, 2-chloro-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, 6-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-nicotinic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid pyridin-2-ylamide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid pyridin-4-ylamide, 5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-pyridine-2-carboxylic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid pyridin-3-ylamide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-iodo-3,5dimethyl-phenyl)-amide, 4-{[(2R,3S,4R,5S)-4-(4-Chloro-2-fluoro-phenyl)-3-(3-chloro-2 fluoro-phenyl)-4-cyano-5-(2,2-dimethyl-propyl)-pyrrolidine-2-carbonyl]-amino}-2-fluoro-benzoic acid tert-butyl ester, 4-{[(2R,3S,4R,5S)-4-(4-Chloro-2-fluoro-phenyl)-3-(3-chloro-2 fluoro-phenyl)-4-cyano-5-(2,2-dimethyl-propyl)-pyrrolidine-2-carbonyl]-amino}-2-fluoro-benzoic acid, 4-{[(2R,3S,4R,5S)-4-(4-Chloro-2-fluoro-phenyl)-3-(3-chloro-2 fluoro-phenyl)-4-cyano-dimethyl-propyl)-pyrrolidine-2-carbonyl]-amino}-3-fluoro-benzoic acid, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-trifluoromethyl-benzoic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-iodo-2-trifluoromethoxy-phenyl)-amide, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-trifluoromethoxy-benzoic acid methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-trifluoromethoxy-benzoic acid, 6-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-nicotinic acid, 6-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-nicotinic acid methyl ester, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (6-iodo-pyridin-3-yl)-amide, 5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-pyridine-2-carboxylic acid methyl ester, 4-{[(2R,3S,4R,5 S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (6-carbamoyl-naphthalen-2-yl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-chloro-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-trifluoromethyl-phenyl)-amide, 5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-pyridine-2-carboxylic acid, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-fluoro-benzoic acid methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-chloro-benzoic acid methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-chloro-benzoic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-2-fluoro-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-2-methoxy-phenyl)-amide, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2,5-difluoro-benzoic acid methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2,5-difluoro-benzoic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (3,5-difluoro-4-iodo-phenyl)-amide, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2,6-difluoro-benzoic acid, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-hydroxy-benzoic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-methoxy-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-trifluoromethoxy-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-fluoro-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-2-chloro-phenyl)-amide, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-fluoro-5-methoxy-benzoic acid methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-fluoro-5-methoxy-benzoic acid, 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-4-methyl-pentanoic acid, chiral 2-(4-{[(2 S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-2-methyl-propionic acid methyl ester, chiral 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-2-methyl-propionic acid, chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1-methyl-1-methylcarbamoyl-ethyl)-phenyl]-amide, chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid {4-[1-(3-hydroxy-propylcarbamoyl)-1-methyl-ethyl]-phenyl}amide, and chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1-carbamoyl-1-methyl-ethyl)-phenyl]-amide.

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkylcarbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the cycloalkyl, cycloalkenyl, aryl, heteroaryl and heterocycle rings are halogen, lower alkoxy, lower alkyl, hydroxycarbonyl, carboxy, carboxy lower alkoxy, oxo and CN. Preferred substituents for alkyl are alkoxy and N(lower alkyl)$_2$.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or Spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl. Where the aryl group is bicyclic a preferred group is 1,3-dioxo-2,3-dihydro-1H-isoindol-5-yl group.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole substituted or unsubstituted triazolyl and substituted or unsubstituted tetrazolyl.

In the case of aryl or heteroaryl which are bicyclic it should be understood that one ring may be aryl while the other is heteroaryl and both being substituted or unsubstituted.

"Heterocycle" or "heterocyclic ring" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like which in turn can be substituted. "Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, iso-propoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable derivative," such as pharmaceutically acceptable salts & esters, carrier, excipient, means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds.[32]

A preferred compound for use in the present invention is 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid

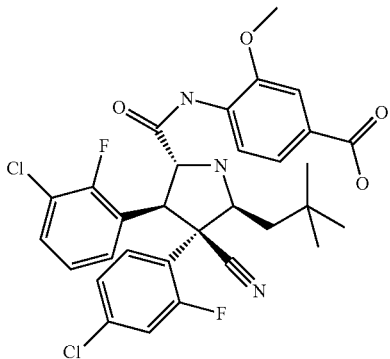

Molecular Weight = 616.4973
Molecular Formula = C31H29Cl2F2N3O4

The compounds of formula III are used in the present invention in a method to determine or predict responsiveness of a patient to the compounds and to method for treating a patient with a compound of formula III, and general pharmaceutically acceptable derivatives thereof, formula III.

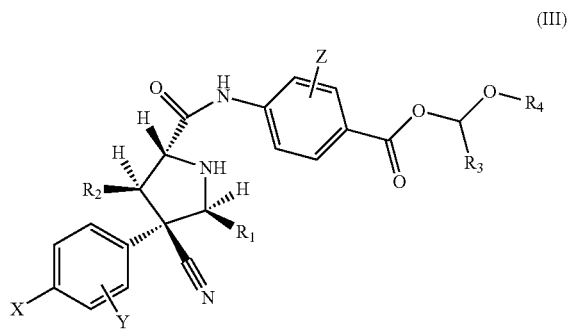

(III)

wherein X, Y, Z, $R_1$, $R_2$, $R_3$ and $R_4$ are as described herein and enantiomers and pharmaceutically acceptable salts and esters thereof.

In one embodiment there are provided compounds of formula III used in the invention.

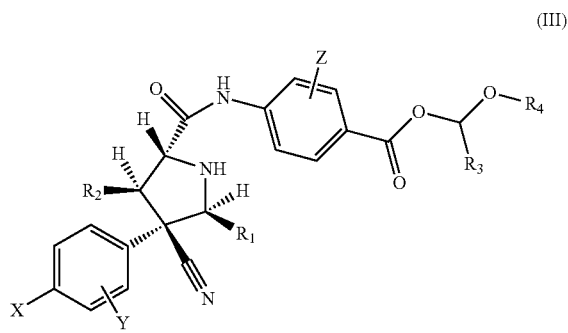

(III)

wherein

X is selected from the group consisting of H, F, Cl, Br, I, cyano, nitro, ethynyl, cyclopropyl, methyl, ethyl, isopropyl, vinyl and methoxy, Y is one to four group(s) independently selected from the group consisting of H, F, Cl, Br, I, CN, OH, nitro, lower alkyl, cycloalkyl, lower alkoxy, lower alkenyl, cycloalkenyl, lower alkynyl, Z is lower alkoxy, $R_1$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl, $R_2$ is a substituted phenyl selected from:

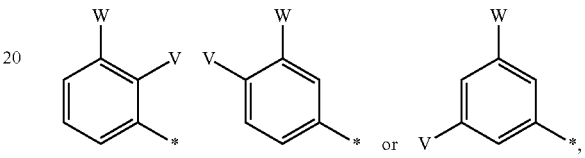

W is F, Cl or Br,
V is H or F,
$R_3$ is selected from the group consisting of hydrogen, lower alkyl or substituted lower alkyl,
$R_4$ is selected from the group consisting of

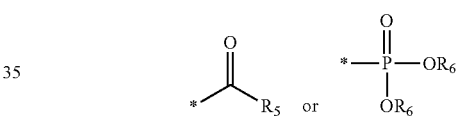

$R_5$ is selected from the group consisting of lower alkyl, substituted lower alkyl, heterocycle, substituted heterocycle, cycloalkyl, substituted cycloalkyl, natural and unnatural amino acids, —(OCH$_2$CH$_2$)$_n$—OH, —(OCH$_2$CH$_2$)$_n$—OCH$_3$, —(NCH$_2$CH$_2$)$_n$—OH, —(NCH$_2$CH$_2$)$_n$—OCH$_3$ and —(OCH$_2$CH$_2$)$_n$—OP(O)(OR$_6$)$_2$, wherein n is from 3 to 60, preferably from 3 to 45, $R_6$ is hydrogen or benzyl; or a pharmaceutically acceptable salt or ester thereof.

Furthermore, as used herein
X is selected from H, F or Cl,
Y is selected from H, F or Cl,
$R_1$ is lower alkyl or substituted lower alkyl,
$R_3$ is hydrogen or lower alkyl,
$R_5$ is selected from the group consisting of lower alkyl, substituted lower alkyl,
natural and unnatural amino acids, —(OCH$_2$CH$_2$)$_n$—OH, —(OCH$_2$CH$_2$)$_n$—OCH$_3$, —(NCH$_2$CH$_2$)$_n$—OH, —(NCH$_2$CH$_2$)$_n$—OCH$_3$, —(OCH$_2$CH$_2$)$_n$—OP(O)(OR$_6$)$_2$, wherein n is from 3 to 60, preferably from 3 to 45, and
$R_6$ is hydrogen; or
a pharmaceutically acceptable salt thereof.

Furthermore, compounds as used herein, wherein
X is selected from H, F or Cl;
Y is selected from H, F or Cl;
Z is C1-6 alkoxy;
$R_1$ is C1-6 alkyl;

R<sub>2</sub> is

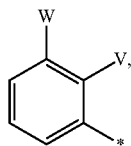

wherein
W is F, Cl or Br;
V is H or F;
R$_3$ is hydrogen or C1-6 alkyl;
R$_4$ is —C(O)—R$_5$; wherein
R$_5$ is selected from the group consisting of —(OCH$_2$CH$_2$)$_n$—OH; —(OCH$_2$CH$_2$)$_n$—OCH$_3$; and —(OCH$_2$CH$_2$)$_n$—OP(O)(OR$_6$)$_2$, wherein n is from 3 to 60, and R$_6$ is hydrogen; or
a pharmaceutically acceptable salt thereof.

More specifically n is from 3 to 55, more preferably n is from 3 to 45. Within this embodiment, compounds wherein R$_5$ is —(OCH$_2$CH$_2$)$_n$—OCH$_3$ and n is from 40 to 60 are especially preferred.

Specific compounds used in the present invention are selected from
1-(Ethyl(isopropyl)carbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid di-tert-butoxy-phosphoryloxymethyl ester,
4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[bis-(2-methoxy-ethyl)-carbamoyloxy]-ethyl ester,
4-Methyl-piperazine-1-carboxylic acid 1-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoyloxy)-ethyl ester,
1-Acetoxyethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
Rac-1-(isobutyryloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid acetoxymethyl ester,
1-(Cyclohexyloxycarbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
Rac-1-(isopropoxycarbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
1-(4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy)ethyl morpholine-4-carboxylate,
Morpholine-4-carboxylic acid (R)-1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-ethyl ester,
Morpholine-4-carboxylic acid (S)-1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-ethyl ester,
Rac-1-tert-butyl 4-(1-(4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)ethyl) piperazine-1,4-dicarboxylate,
Piperazine-1-carboxylic acid 1-(4-{[(2R,3S,4R,5S)-4-(4-chloro-2-fluoro-phenyl)-3-(3-chloro2-fluoro-phenyl)-4-cyano-5-(2,2-dimethyl-propyl)-pyrrolidine-2-carbonyl]-amino}-3-methoxy-benzoyloxy)-ethyl ester di-hydrochloride,
Rac-1,1-Dioxo-thiomorpholine-4-carboxylic acid 1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoyloxy)-ethyl ester,
4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-(2,2-dimethyl-[1,3]dioxolan-4-ylmethylcarbamoyloxy)-ethyl ester,
4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 1-(2,3-dihydroxy-propylcarbamoyloxy)-ethyl ester,
1-(Tetrahydro-2H-pyran-4-ylcarbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-{2-[2-(2-methoxy-ethoxy)-ethoxy]-ethoxycarbonyloxy}-ethyl ester,
4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-methoxy-ethoxy)-ethoxy]-ethoxy}-ethoxycarbonyloxy)-ethyl ester,
4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[2-(2-{2-[2-(2-methoxy-ethoxy)-ethoxy]-ethoxy}-ethoxy)-ethoxycarbonyloxy]-ethyl ester,
21-oxo-2,5,8,11,14,17,20,22-octaoxatetracosan-23-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester,
1-(2-(Benzyloxy)-2-oxoethylcarbamoyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate,
2-((1-(4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy)ethoxy)carbonylamino)acetic acid,
(S)-2-[1-(4-{[(2R,3S,4R,5S)-3-(3-Chloro-2-fluoro-phenyl)-4-(4-chloro-2-fluoro-phenyl)-4-cyano-5-(2,2-dimethylpropyl)-pyrrolidine-2-carbonyl]-amino}-3-methoxy-benzoyloxy)-ethoxycarbonylamino]-pentanedioic acid, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-((S)-1-carboxy-ethylcarbamoyloxy)-ethyl ester, 2-(((4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy)methoxy)-carbonylamino)acetic acid, (S)-Dibenzyl 2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)-pentanedioate, (S)-2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)-methoxy)carbonylamino)pentanedioic acid, 15-methyl-12-oxo-2,5,8,11,13-pentaoxahexadecan-14-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 3-Oxo-2,4,7,10,13-pentaoxatetradecyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 3-Oxo-2,4,7,10,13,16,19-heptaoxaicosyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl ester, 3-Oxo-2,4,7,10,13-pentaoxatetradecyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 27-Oxo-2,5,8,11,14,17,20,23,26,28-decaoxatriacontan-29-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 24-Oxo-2,5,8,11,14,17,20,23,25-nonaoxaheptacosan-26-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl amide, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl amide, (S)-2-(((4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoyloxy)methoxy)carbonylamino)propanoic acid, Dibenzyl 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-phosphonooxy-ethoxy)-ethoxy]-ethoxy}-ethoxycarbonyloxymethyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid 2-{2-[2-(2-phosphonooxy-ethoxy)-ethoxy]-ethoxy}-ethoxycarbonyloxymethyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid phosphonooxymethyl ester; compound with trifluoro-acetic acid, 1-(((3aR,5R,6S,6aR)-5-((R)-2,2-dimethyl-1,3-dioxolan-4-yl)-2,2-dimethyltetrahydrofuro[3,2-d][1,3]dioxol-6-yloxy)carbonyloxy)ethyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[(2R,3R,4R,5S)-2-((R)-1,2-dihydroxy-ethyl)-4,5-dihydroxy-tetrahydro-furan-3-yloxycarbonyloxy]-ethyl ester, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-dibenzyloxyphosphoryloxy-ethoxy)-ethoxy]-ethoxy}-ethoxycarbonyloxy)-ethyl ester and 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-phosphonooxy-ethoxy)-ethoxy]-ethoxy}-ethoxycarbonyloxy)-ethyl ester.

A specific compound used in the present invention is 2-((1-(4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy)ethoxy)carbonylamino)acetic acid.

Another specific compound used in the present invention is 2-(((4-((2R,3S,4R,5S)-3-(3-Chloro-2-fluorophenyl)-4-(4-chloro-2-fluorophenyl)-4-cyano-5-neopentylpyrrolidine-2-carboxamido)-3-methoxybenzoyloxy)methoxy)-carbonylamino)acetic acid.

A further compound used in the present invention is 3-Oxo-2,4,7,10,13,16,19-heptaoxaicosyl 4-((2R,3S,4R,5S)-

3-(3-chloro-2-fluorophenyl)-4-(4-chloro-2-fluorophenyl)-4-cyano-5-neopentylpyrrolidine-2-carboxamido)-3-methoxy-benzoate.

A specific compound used in the present invention is 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2000).

A specific compound used in the present invention is 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2200)

A specific compound used in the present invention is 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-methyl ester (mPEG, average MW, ~2000).

A specific compound used in the present invention is 3-Oxo-2,4,7,10,13-pentaoxatetradecyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxy-benzoate;

A specific compound used in the present invention is 27-Oxo-2,5,8,11,14,17,20,23,26,28-decaoxatriacontan-29-yl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate.

A specific compound used in the present invention is 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-[(2R,3R,4R,5S)-2-((R)-1,2-dihydroxy-ethyl)-4,5-dihydroxy-tetrahydro-furan-3-yloxycarbonyloxy]-ethyl ester.

In another specific compound used in the present invention is 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-dibenzyloxyphosphoryloxy-ethoxy)-ethoxy]-ethoxy}-ethoxycarbonyloxy)-ethyl ester.

Also a specific compound used in the present invention is 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-(2-{2-[2-(2-phosphonooxy-ethoxy)-ethoxy]-ethoxy}-ethoxycarbonyloxy)-ethyl ester.

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2000)

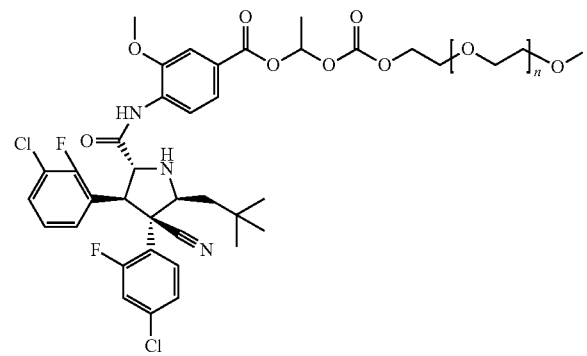

Average MW: ~2695

In Chloroethyl chloroformate (Oakwood, 1.46 g, 1.1 mL, 10.2 mmol) is reacted with poly(ethylene glycol) monomethyl ether (mPEG) (Aldrich, average MW ~2000, 18.84 g, 9.42 mmol) and pyridine (939 mg, 0.96 mL, 11.9 mmol) in methylene chloride (6 mL) at −78° C. for 3 h to give 1-chloroethyl mPEG carbonate with pyridine hydrochloride (1:1). This 1-chloroethyl mPEG carbonate (4.67 g, 4.87 mmol) in dimethylformamide (25 mL) is then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (300 mg, 0.487 mmol), as e.g. obtainable via the method disclosed in WO2011/098398, and cesium carbonate (1.97 g, 6.04 mmol) in dimethylformamide (6 mL) overnight to give, after high-performance liquid chromatography purification (10% to 100% acetonitrile in water), 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2000) as a white solid (171.6 mg, 13% yield).

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2200)

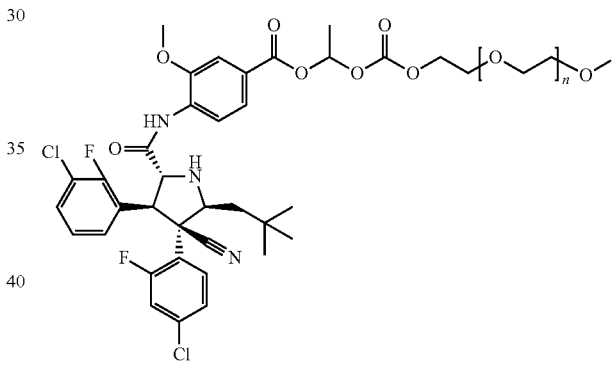

Average MW: ~2900 a) 1-Chloroethyl 2-methoxyethyl carbonate-mPEG (average MW ~2300)

Methoxy-poly(ethylene glycol) (ID Biochem, average MW ~2200 determined by MALDI-TOF MS, 2.5 kg, ~1.14 mol) and lithium carbonate (185 g, 2.5 mol) are charged to a 50-L glass reactor, and dichloromethane (39.8 kg, 30.0 L) was added. The mixture is stirred for 1 hour, and then 1-chloroethyl chloroformate (1.07 kg, 819 mL, 7.5 mol) was added via dropping funnel. With vigorous mixing, a catalytic amount of pyridine (4.94 g, 5.05 mL, 62.5 mmol) is added, and gas evolution was observed. The mixture is stirred at 25 C under $N_2$ for 21 hours. HPLC-CAD analysis showed ~3% mPEG-OH remaining. The reaction mixture is filtered to remove insoluble salts, and then the liquors are polish filtered through a 0.4 micron filter. The liquors are concentrated to remove dichloromethane by vacuum distillation and the solvent exchanged to n-heptane. The resulting slurry in n-heptane is cooled to 0° C. and aged for 1 hour prior to filtering the product as a white powder. The solids are washed with n-heptane then dried at 35° C. in a vacuum oven with $N_2$ purge to yield 2340 g (90%) of 1-chloroethyl 2-methoxyethyl carbonate-mPEG (average MW ~2300).

b) 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]amino}-3-methoxy-benzoic acid 1-mPEG-carbonyloxy-ethyl ester (mPEG, average MW ~2200)

A 12-L flask is charged with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxy-benzoic acid cesium salt (400 g, 533 mmol), 1-chloroethyl 2-methoxyethyl carbonate-mPEG, (avg MW ~2300) (1.51 kg, ~657 mmol), and cesium carbonate (43.4 g, 133 mmol, Eq: 0.25), followed by DMSO (4.00 L). The mixture is stirred and heated to 50° C. for 4 hours. The temperature is adjusted to 30° C. and the reaction stirred for 6 days. Additional 1-chloroethyl 2-methoxyethyl carbonate-mPEG, (avg MW ~2300) (112 g, ~49 mmol) is added, and the mixture heated again to 50° C. for 2 days. HPLC analysis showed ca. 98% conversion. The reaction mixture is cooled to 20° C., then poured into a prepared solution containing water (8.00 L) and hydrochloric acid (26.7 ml, 320 mmol). The resulting solution is stirred for a few minutes, and then the pH adjusted to ~6.5 by addition of $Cs_2CO_3$. The solution is stirred until analysis (HPLC-CAD) showed complete hydrolysis of excess 1-chloroethyl 2-methoxyethyl carbonate-mPEG to methoxy-poly(ethylene glycol). The solution is extracted with dichloromethane (10.6 kg, 8.00 L). The dichloromethane fraction is washed with water (8.00 kg, 8.00 L) four (4) times, and then with brine. The organic phase is concentrated under vacuum to give 1.885 kg crude pasty-solid that contained a mixture of the product and mPEG-OH. This residue is dissolved in isopropyl acetate (26.1 kg, 30.0 L) and then washed with 50% brine solution (1.13 L, prepared from 200 g NaCl in 1.13 L water). The mixture is allowed to settle for 1 h, and then the lower aqueous phase is removed. The remaining isopropyl acetate organic phase is polish filtered through diatomaceous earth. This solution is concentrated by vacuum distillation to provide a solid residue that is re-dissolved in isopropyl acetate (4.0 L). Once a clear solution is achieved, it is cooled to 10° C. and then n-heptane (8.0 L) was slowly added with vigorous mixing. After the first ca. 1.0 L is added, the product begins to precipitate as a fine, white slurry. The remaining n-heptane is added and the suspension stirred at 6-10° C. for 0.5 h. Filtration provided a white powder that is dried in a vacuum oven at 35° C. with $N_2$ purge. The title compound 4-{[(2R,3S,4R,5S)-3-(3-Chloro-2-fluoro-phenyl)-4-(4-chloro-2-fluoro-phenyl)-4-cyano-5-(2 dimethyl-propyl)-pyrrolidine-2-carbonyl]-amino}-3-methoxy-benzoic acid 1-mPEG-carbonyloxy-ethyl ester (mPEG, average MW, 2200) Average MW: ~2900, was obtained in 1128 g (73%) yield, 99.5% purity (LC-CAD).

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkylcarbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the cycloalkyl, cycloalkenyl, aryl, heteroaryl and heterocycle rings are halogen, lower alkoxy, lower alkyl, hydroxycarbonyl, carboxy, carboxy lower alkoxy, oxo and CN. Preferred substituents for alkyl are alkoxy and N(lower alkyl)$_2$.

The term "mPEG" as used herein means methoxy polyethylene glycol, which is commercially available (e.g. Sigma-Aldrich or ID Biochem (Korea)). The molecular weight distribution of mPEG may vary according to the manufacturer and/or batch. In one embodiment of the present invention, mPEG has an average molecular weight (MW) of about 1500 Da to about 3000 Da. In another embodiment of the present invention mPEG has an average MW of about 2000 Da and about 2200 Da. Average MW is determined by MALDI-TOF mass spectrometry.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl. Where the aryl group is bicyclic a preferred group is 1,3-dioxo-2,3-dihydro-1H-isoindol-5-yl group.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole substituted or unsubstituted triazolyl and substituted or unsubstituted tetrazolyl.

In the case of aryl or heteroaryl which are bicyclic it should be understood that one ring may be aryl while the other is heteroaryl and both being substituted or unsubstituted.

In particular, useful in the present invention is, 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2000)

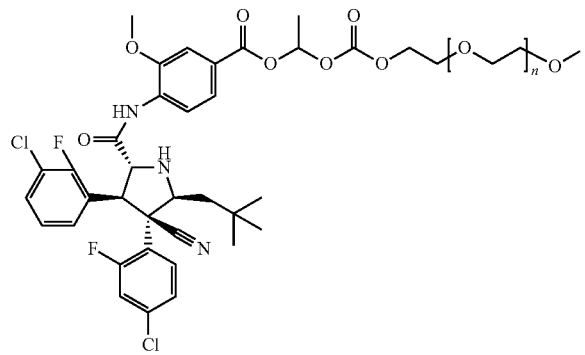

Average MW: ~2695

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2200)

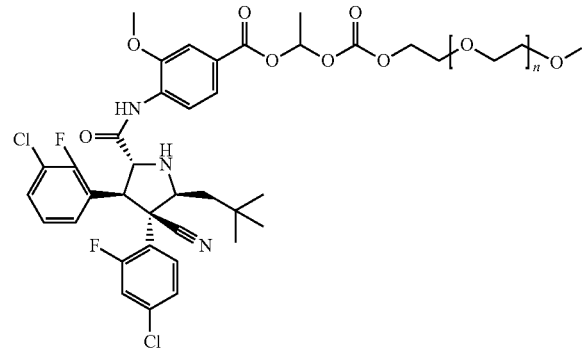

Average MW: ~2900

In a manner similar to the method described in herein, chloroethyl chloroformate (Oakwood, 1.46 g, 1.1 mL, 10.2 mmol) is reacted with poly(ethylene glycol) monomethyl ether (mPEG) (Aldrich, average MW ~2000, 18.84 g, 9.42 mmol) and pyridine (939 mg, 0.96 mL, 11.9 mmol) in methylene chloride (6 mL) at −78° C. for 3 h to give 1-chloroethyl mPEG carbonate with pyridine hydrochloride (1:1). This 1-chloroethyl mPEG carbonate (4.67 g, 4.87 mmol) in dimethylformamide (25 mL) is then reacted with chiral 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (300 mg, 0.487 mmol), as e.g. obtainable via the method disclosed in WO2011/098398, and cesium carbonate (1.97 g, 6.04 mmol) in dimethylformamide (6 mL) overnight to give, after high-performance liquid chromatography purification (10% to 100% acetonitrile in water), 4-{[(2R,3S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2000) as a white solid (171.6 mg, 13% yield).

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2200)

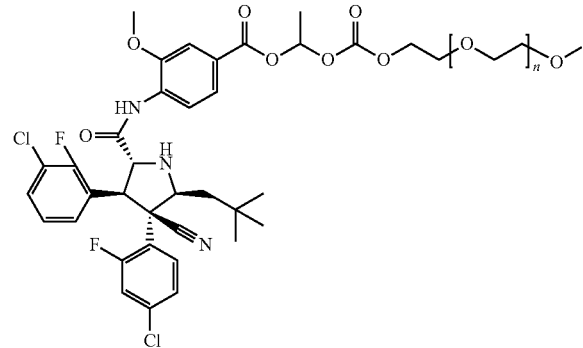

Average MW: ~2900 a) 1-Chloroethyl 2-methoxyethyl carbonate-mPEG (average MW ~2300)

Also, the disease that is potentially treatable based on the MDM2 response is a neoplastic (cancer) disease. Especially preferably, the cancer is selected from the group consisting of breast cancer, prostate cancer, cervical cancer, ovarian cancer, gastric cancer, colorectal cancer (i.e. including colon cancer and rectal cancer), pancreatic cancer, liver cancer, brain cancer, neuroendocrine cancer, lung cancer, kidney cancer, hematological malignancies, melanoma and sarcomas. More especially preferably the cancer is selected from the group consisting of hematological malignancies, prostate cancer, breast cancer, cervical cancer, ovarian cancer, colorectal cancer, melanoma and lung cancer. In an especially preferred embodiment, the cancer is acute myeloid leukemia (AML).

In a further aspect, the invention relates to a method of treating a neoplastic disease, cancer, in a patient in need thereof, comprising measuring a level in a sample from the patient to obtain a value or values representing this level, and treating the subject with a compound of general formula I or a pharmaceutically acceptable derivative thereof as defined above.

In yet another aspect, the invention relates to a kit for predicting the response to a compound of formula or a pharmaceutically acceptable derivative thereof, as defined above, comprising reagents necessary for measuring the level in a sample. More preferably the kit also comprises a comparator module which comprises a standard value or set of standard values to which the level of response in the sample is compared. The kit may also comprise a captive reagent.

More preferably the kit comprises a compound of formula I, II, III or combination thereof or a pharmaceutically acceptable derivative.

The present invention identifies a gene expression signature (mRNA) panel based on in vitro and clinical data that identify patients most likely to respond to MDM2 antagonist therapy. The mRNA signature is characterized by up-regulations of at least three genes, specifically MDM2, XPC (xeroderma pigmentosum, complementation group C), BBC3 (BCL2 binding component 3) and down-regulation of CDKN2A (cyclin-dependent kinase inhibitor 2A).

The present invention identifies a 4-gene expression signature (mRNA) for identifying responses to MDM2 antagonist.

The baseline expression levels of MDM2, BBC3, CDKN2A, and XPC yield a composite score that discriminates between cell lines and patient-derived clinical specimens that are resistant to therapy, and identifies those that are sensitive (responsive) to the therapy.

As such, the present invention relates to a method for identifying sensitivity to MDM2 antagonist therapy. Furthermore, the present invention relates to a method for treating a cancer patient with an MDM2 antagonist by testing the sensitivity of the patient before hand by the gene signature (mRNA) panel, more specifically a panel including MDM2, and more specifically a 4-gene expression system.

The present invention further provides the predictive signature utilizing mRNA values in determining the effectiveness of MDM2 antagonist therapy to cancers, in particular, AML.

The present invention relates to the use of a gene panel containing at least the MDM2 gene as predictive mechanism for determining a patent's response to a disease, particularly cancer, more particularly acute myeloid leukemia (AML), when a patient is to be treated with an MDM2 antagonist.

More particularly, the present invention relates to the use of a four-gene panel in order to determine a patient's response to a disease, particularly AML, when a patient is to be treated with an MDM2 antagonist.

(a) The heatmap of the four gene mRNAs (green corresponds to lower expression, red to higher expression) associated with MDM2 antagonist response for the most sensitive (IC50<=1; purple) and resistant (IC50>=10 yellow) cell lines. For each cell line TP53 mutation features are at the top of the heatmap shown in black (present) or grey (absent). The natural log IC50 values are represented at the bottom.

(b) The boxplot of the 4-gene mRNA signature score for the most sensitive (IC50<=1) and resistant (IC50>=10) cell lines.

Figure 3:
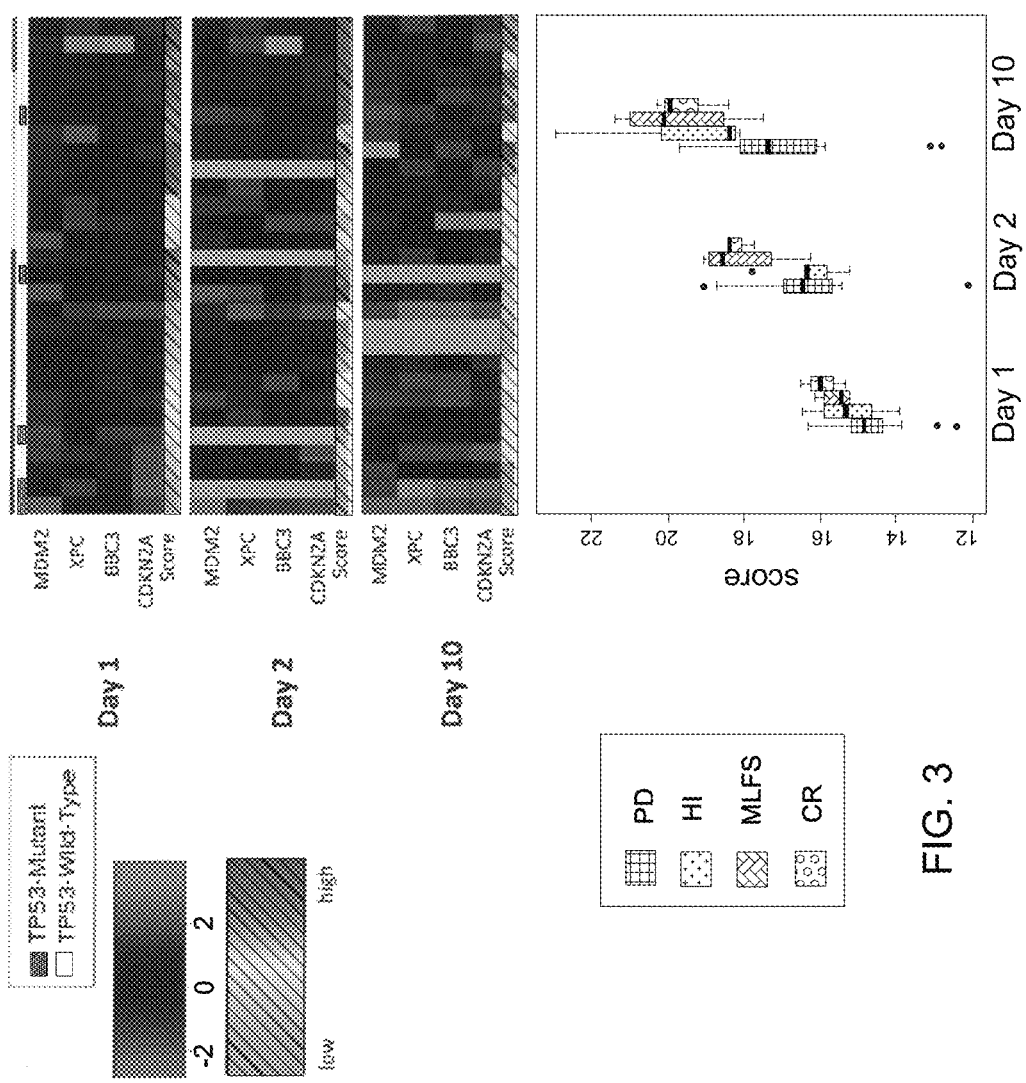

FIG. 3: MDM2 antagonist response mRNA signature in AML trial.

(a) The heatmap of the four gene mRNAs (blue corresponds to lower expression, red to higher expression) associated with MDM2 antagonist response for the 28 evaluated patients. For each patient TP53 mutation features are at the top of the heatmap shown in black (present) or grey (absent). The clinical efficacy groups are represented at the bottom.

(b) The boxplot of the 4-gene mRNA signature score for 28 evaluated patients.

Figure 4A:
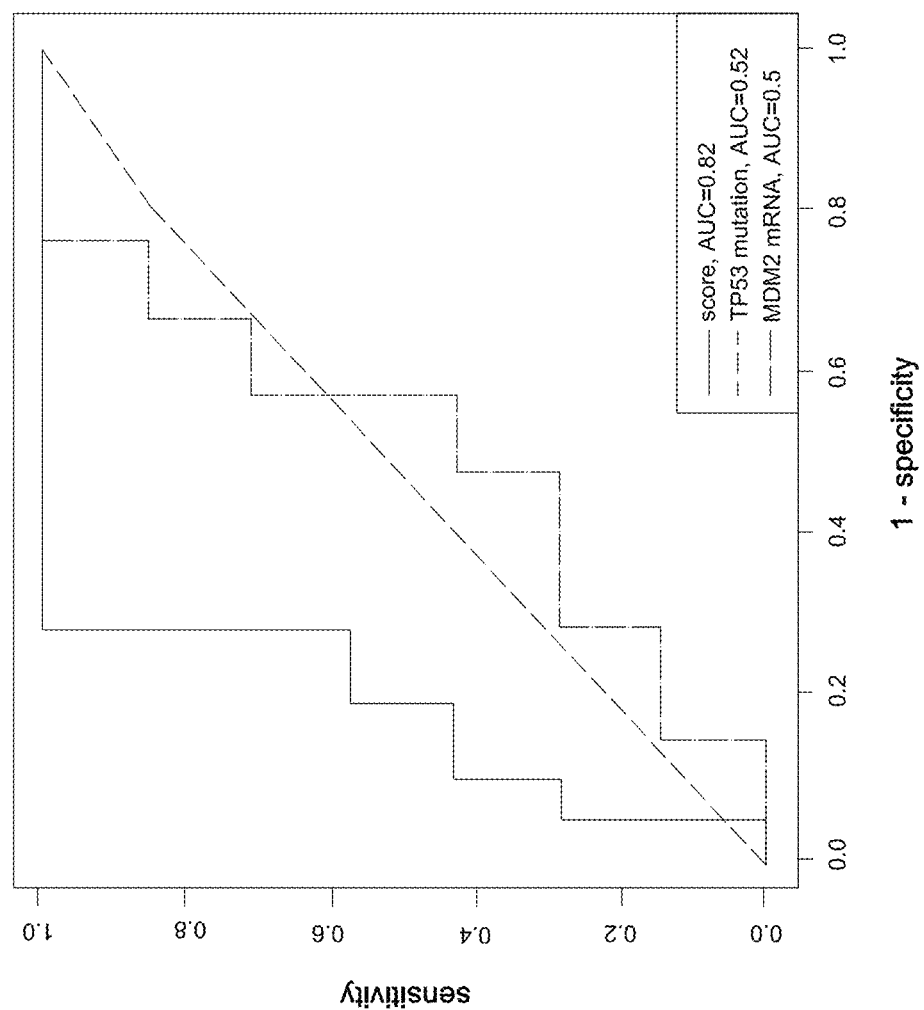

FIGS. 4A and 4B: The area under the curve (AUC) of receiver operating characteristic (ROC) curves of the three biomarks/biosignatures in AML trial The four gene mRNA signature score (black curve) showed AUC 0.82, MDM2 mRNA single biomarker (blue curve) showed AUC 0.5; P53 mutation status biomarker (green cruve) showed AUC 0.52.

DETAILED DESCRIPTION OF THE INVENTION

Establishment of MDM2 Antagonist Therapy Predictive Signature in Cancer Cell Line Collections To generate an MDM2 antagonist therapy predictive signature, the response of MDM2 antagonist therapy in vitro with gene expression profiling (FIG. 1) is combined. A bank of 287 human cancer cell lines, collectively termed the Cell Lines for Oncology/Chugai ACcumulative Tumour EncycLopedia (CELLO/CACTEL), representing a broad array of diverse human cancer tumor types are subject to evaluation using several high-throughput genomic technology platforms. The mutational status of nucleic acids from each cell line is determined by exome sequencing. Messenger RNA (mRNA) expression levels at baseline, prior to MDM2 antagonist therapy, are obtained via RNA sequencing. MDM2 antagonist therapy COMPOUND A, sometimes referred to herein as RG7112, responses are obtained by assays known to those skilled in the art such as RNA sequencing and microarray measurement using Gene Chip Human Genome U133 Plus 2.0 Array. The MDM2 therapy responses are obtained by high throughout screening assays. Depending on their responses to COMPOUND A these cell lines are classified as either sensitive, defined as IC50<=1, or resistant, defined as IC50>=10.

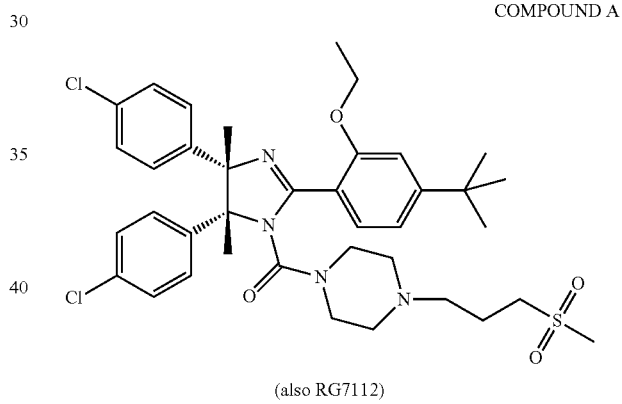

COMPOUND A (also RG7112)

TABLE 1

CELLO/CACTEL Cell Lines

| Cell Lines | Tissue | Origin | IC50 | TP53 |
|---|---|---|---|---|
| 22Rv1 | Prostate | Carcinoma | 0.97 | Mutant |
| A-172 | Brain | Glioblastoma | 0.58 | Wild type |
| A-375 | Skin | Melanoma, malignant | 0.32 | Wild type |
| A549 | Lung | Carcinoma, squamous cell | 0.86 | Wild type |
| ACHN | Kidney | Adenocarcinoma, renal cell | 0.29 | Wild type |
| AGS | Stomach | Adenocarcinoma, gastric | 0.13 | Wild type |
| Caki-1 | Kidney | Carcinoma, clear cell | 0.37 | Wild type |
| D341 Med | Brain, cerebellum | Medulloblastoma | 0 | Wild type |
| HCT116 | Intestine, large; colon | Carcinoma, colorectal | 0.5 | Wild type |

TABLE 1-continued

CELLO/CACTEL Cell Lines

| Cell Lines | Tissue | Origin | IC50 | TP53 |
|---|---|---|---|---|
| HepG2 | Liver | Carcinoma, hepatocellular | 0.18 | Wild type |
| Hs 38·T | Ovary | Teratoma | 0.73 | Wild type |
| HT-1080 | Connective tissue | Fibrosarcoma | 0.058 | Wild type |
| HT-1197 | Urinary, bladder | Carcinoma, urinary bladder, papillary | 0.19 | Wild type |
| IM-9 | Lymphocyte B, peripheral blood | Myeloma, multiple | 0.14 | Wild type |
| IMR-32 | Brain | Neuroblastoma (Glioma, neuroblastoma) | 0.43 | Wild type |
| KMS-12-BM | Bone marrow | Myeloma, multiple | 0 | Mutant |
| KMS-21BM | Bone marrow | Myeloma, multiple | 0 | Wild type |
| KMS-26 | Lymphocyte | Myeloma | 0.45 | Mutant |
| LCLC-103H | Lung | Carcinoma, large cell, non-small cell lung cancer | 0.7 | Mutant |
| LN-18 | Brain, temporal lobe | Glioblastoma | 0.67 | Mutant |
| LNCaP clone FGC | NA | NA | 0.17 | Wild type |
| LS 174T | Intestine, large; colon | Adenocarcinoma, colorectal | 0.59 | Wild type |
| LS513 | Intestine, large; caecum | Carcinoma, colorectal | 0.49 | Wild type |
| MC/CAR | Lymphocyte B, peripheral blood | Myeloma, plasmacytoma | 0.69 | Wild type |
| MCF7 | Breast, mammary gland | Adenocarcinoma, mammary gland, breast | 0.75 | Wild type |
| MKN-45 | Stomach | Adenocarcinoma | 0.18 | Mutant |
| MKN-74 | Muscle, smooth, stomach | Carcinoma, gastric | 0.88 | Wild type |
| MOLM-13 | Blood | Leukemia, acute myeloid | 0.19 | Wild type |
| MV-4-11 | Blood | Leukemia, acute monocytic | 0 | Wild type |
| NCI-H2122 | Lung | Adenocarcinoma | 0.16 | Mutant |
| NCI-H226 | Lung | Carcinoma, squamous cell | 0.13 | Mutant |
| NCI-H28 | null | Mesothelioma | 0.46 | Wild type |
| NCI-H460 | Lung | Carcinoma | 0.88 | Wild type |
| NCI-H929 | Lymphocyte B, bone marrow | Myeloma, plasmacytoma | 0.3 | Wild type |
| NKM-1 | Lymphocyte | Leukemia, acute myeloid | 0.32 | Wild type |
| NUGC-4 | Stomach | Adenocarcinoma | 0.38 | Wild type |
| PA-1 | Ovary | Carcinoma, ovary | 0.62 | Wild type |
| PC-9 | Lung | Adenocarcinoma | 0.69 | Mutant |
| RKO | Intestine, large; colon | Carcinoma, colorectal | 0 | Wild type |
| RPMI-2650 | Nasal septum | Carcinoma, squamous cell | 0.77 | Wild type |
| SH-SY5Y | Brain | Neuroblastoma (Glioma, neuroblastoma) | 0.75 | Wild type |
| SK-HEP-1 | Liver | Hepatoma, Hepatocellular carcinoma | 0.22 | Wild type |
| SK-MEL-1 | Skin | Melanoma, malignant | 0.75 | Wild type |
| SK-N-SH | Brain | Neuroblastoma (Glioma, neuroblastoma) | 0.21 | Wild type |
| SNU-1 | Stomach | Carcinoma, gastric | 0.37 | Wild type |
| SR | Lymphocyte | Lymphoma, large cell | 0.043 | Wild type |
| SW780 | Urinary, bladder | Carcinoma, urinary bladder, transitional cell carcinoma | 0.97 | Wild type |
| U-87 MG | Brain | Glioblastoma | 0.18 | Wild type |
| WERI-Rb-1 | Eye, retina | Retinoblastoma | 0.67 | Wild type |
| Y79 | Eye, retina | Retinoblastoma | 0.61 | Wild type |

TABLE 1-continued

CELLO/CACTEL Cell Lines

| Cell Lines | Tissue | Origin | IC50 | TP53 |
|---|---|---|---|---|
| ZR-75-1 | Breast, mammary gland | Carcinoma, ductal | 0.076 | Wild type |
| 5637 | Urinary, bladder | Carcinoma, urinary bladder, papillary | 8.5 | Mutant |
| 143B | Bone | Osteosarcoma | 15 | Mutant |
| 647-V | Urinary tract, urothelium | Carcinoma, urinary bladder, transitional cell carcinoma | 17 | Mutant |
| 786-O | Kidney | Adenocarcinoma, renal cell | 9.5 | Mutant |
| A-204 | Muscle | Rhabdomyosarcoma | 8.4 | Mutant |
| A2058 | Skin | Melanoma | 17 | Mutant |
| A-431 | Skin, epidermis | Carcinoma, epidermoid | 9.5 | Mutant |
| ABC-1 | Lung | Adenocarcinoma | 9.9 | Mutant |
| ARH-77 | Lymphocyte B, peripheral blood | Leukemia, plasma cell | 17 | Mutant |
| BT-20 | Breast, mammary gland | Adenocarcinoma, mammary gland, breast | 3.6 | Mutant |
| C32 | Skin | Melanoma | 3 | Wild type |
| Calu-1 | Lung | Carcinoma, lung epidermoid OR Carcinoma, epidermoid pulmonary | 14 | Wild type |
| Calu-3 | Lung | Adenocarcinoma | 11 | Mutant |
| Calu-6 | Lung | Carcinoma, anaplastic | 17 | Mutant |
| Capan-2 | Pancreas | Adenocarcinoma | 9.1 | Mutant |
| CCRF-CEM | Lymphocyte T, peripheral blood | Leukemia, acute lymphoid | 9.7 | Mutant |
| CEM/C2 | Lymphocyte T, peripheral blood | Leukemia, acute lymphoid | 9.3 | Mutant |
| CFPAC-1 | Pancreas | Adenocarcinoma, ductal, cystic fibrosis | 5.7 | Mutant |
| CMK-11-5 | Lymphocyte | Leukemia, acute megakaryoblastic | 9.6 | Mutant |
| COLO 201 | Intestine, large; colon | Adenocarcinoma, colorectal | 10 | Mutant |
| COLO 205 | Intestine, large; colon | Adenocarcinoma, colorectal | 9.1 | Mutant |
| COLO 320DM | Intestine, large; colon | Adenocarcinoma, colorectal | 12 | Mutant |
| COLO-824 | Breast | Carcinoma | 15 | Wild type |
| D-283MED | NA | NA | 1.2 | Wild type |
| Daoy | Brain, cerebellum | Medulloblastoma, desmoplastic cerebellar | 9.7 | Mutant |
| Detroit 562 | Pharynx | Carcinoma | 6.2 | Mutant |
| DLD-1 | Intestine, large; colon | Adenocarcinoma | 5.1 | Mutant |
| DMS 114 | Lung | Carcinoma, classic small cell lung cancer | 10 | Mutant |
| DU145 | Prostate | Carcinoma, prostate | 1 | Mutant |
| DU-4475 | Breast, mammary gland | Carcinoma | 2.1 | Wild type |
| EGI-1 | Bile duct | Carcinoma, bile duct OR Cholangiocarcinoma | 9 | Mutant |
| ES2 | Ovary | Carcinoma, clear cell | 3.3 | NA |
| HARA-B | Lung | Carcinoma, squamous cell | 10 | Mutant |
| HCC1143 | Breast, mammary gland | Carcinoma, primary ductal | 12 | Mutant |
| HCC1187 | Breast, mammary gland | Carcinoma, primary ductal | 12 | Mutant |
| HCC1500 | Breast, mammary gland | Carcinoma, primary ductal | 1 | Wild type |
| HCC1569 | Breast, mammary gland | Carcinoma, primary metaplastic | 15 | Mutant |
| HCC1599 | Breast, mammary gland | Carcinoma, primary ductal | 12 | Mutant |
| HCC1806 | Breast, mammary gland | Carcinoma, primary acantholytic squamous cell | 11 | Mutant |
| HCC1937 | Breast | Carcinoma, ductal | 15 | NA |
| HCC1954 | Breast, mammary gland | Carcinoma, ductal | 12 | Mutant |
| HCC366 | Lung | Adenocarcinoma, squamous cell, non-small cell lung cancer | 8.7 | Mutant |
| HCC38 | Breast, mammary gland | Carcinoma, primary ductal | 12 | Mutant |
| HCC827 | Lung | Adenocarcinoma | 8.9 | Mutant |
| HCT-15 | Intestine, large; colon | Adenocarcinoma, colorectal | 7.6 | Mutant |
| HCT-8 | Intestine, large; colon | Adenocarcinoma, colorectal, ileocecal | 16 | Wild type |
| HEC-151 | Uterus | Adenocarcinoma, malignant, endometroid carcinoma | 2.2 | Mutant |
| HEC-1-A | Uterus, endometrium | Adenocarcinoma | 16 | Mutant |
| HEL | Lymphocyte, peripheral blood | Erythroleukemia OR Leukemia, erythroid | 17 | Mutant |
| Hep3B | Liver | Carcinoma, hepatocellular | 6.7 | Mutant |
| HL-60 | Blood | Leukemia, acute promyeloid | 7 | Mutant |
| HMCB | Skin | Melanoma | 15 | Mutant |
| HPAC | Pancreas | Adenocarcinoma | 4.6 | Mutant |
| HPAF-II | Pancreas | Adenocarcinoma | 10 | Mutant |
| Hs 578T | Breast, mammary gland | Carcinoma | 8.8 | Mutant |
| Hs 766T | Pancreas | Carcinoma | 17 | Mutant |
| HT-1376 | Urinary, bladder | Carcinoma | 16 | Mutant |
| HT-29 | Intestine, large; colon | Adenocarcinoma | 7.4 | Mutant |

TABLE 1-continued

CELLO/CACTEL Cell Lines

| Cell Lines | Tissue | Origin | IC50 | TP53 |
|---|---|---|---|---|
| HuH-28 | Gall bladder | Carcinoma, bile duct OR Cholangiocarcinoma | 15 | Mutant |
| Huh-7 | Liver | Hepatoma, Hepatocellular carcinoma | 10 | Mutant |
| HUP-T4 | Pancreas | Carcinoma, pancreatic | 17 | Mutant |
| JIMT-1 | Breast | Carcinoma | 11 | Mutant |
| K-562 | Bone marrow | Leukemia, chronic myeloid | 16 | Mutant |
| KATO-III | Stomach | Carcinoma, gastric | 9.7 | Mutant |
| KELLY | Brain | Neuroblastoma (Glioma, neuroblastoma) | 15 | Mutant |
| KG-1 | Bone marrow | Leukemia | 15 | Mutant |
| KG-1a | Bone marrow | Leukemia, acute myeloid | 9 | Mutant |
| KHM-1B | Lymphocyte | Myeloma, multiple | 6.9 | Wild type |
| KMS-11 | Lymphocyte | Myeloma, multiple | 12 | Wild type |
| KMS-12-PE | Plasma | Myeloma, multiple | 5.3 | Mutant |
| KMS-20 | Lymphocyte | Myeloma | 13 | Mutant |
| KMS-28BM | Lymphocyte | Myeloma | 9 | Mutant |
| KMS-34 | Lymphocyte | Myeloma | 9.8 | Mutant |
| KYSE-150 | Esophagus | Carcinoma, squamous cell | 3 | Mutant |
| KYSE-520 | Esophagus | Carcinoma, squamous cell | 10 | Mutant |
| LoVo | Intestine, large; colon | Adenocarcinoma, colorectal | 1.3 | Wild type |
| LP-1 | Lymphocyte, peripheral blood | Myeloma, multiple | 4.4 | Mutant |
| LS1034 | Intestine, large; caecum | Carcinoma, colorectal | 5.7 | Mutant |
| LS411N | Intestine, large; caecum | Carcinoma, colorectal | 16 | Mutant |
| MCF10DCIS•com | Breast | Carcinoma | 1.4 | Wild type |
| MDA-MB-231 | Breast, mammary gland | Adenocarcinoma | 17 | Mutant |
| MDA-MB-435S | Skin | Melanoma | 12 | Mutant |
| MDA-MB-468 | Breast, mammary gland | Adenocarcinoma, mammary gland, breast | 10 | Mutant |
| ME-180 | Cervix | Carcinoma, epidermoid | 9.3 | Wild type |
| MEG-01 | null | Leukemia, chronic myeloid | 17 | Mutant |
| MFM-223 | Breast, mammary gland | Carcinoma, ductal | 17 | Mutant |
| MG-63 | Bone | Osteosarcoma | 16 | Mutant |
| MKN-1 | Muscle, smooth, stomach | Carcinoma, squamous cell | 15 | Mutant |
| MKN-28 | Stomach | Carcinoma, gastric | 8.1 | Mutant |
| NB-4 | Myeloblast | Leukemia, acute promyeloid | 4.7 | Mutant |
| NCCIT | Germ cell, gametocyte | Teratocarcinoma | 11 | Mutant |
| NCI-H1048 | Lung | Carcinoma, small cell lung cancer | 9.4 | Mutant |
| NCI-H1299 | Lung | Carcinoma, non-small cell lung cancer | 15 | Mutant |
| NCI-H1395 | Lung | Adenocarcinoma | 1.3 | Wild type |
| NCI-H1437 | Lung | Adenocarcinoma, non-small cell lung cancer | 10 | Mutant |
| NCI-H146 | Lung | Carcinoma, small cell lung cancer | 8.3 | Mutant |
| NCI-H1568 | NA | NA | 9.6 | Mutant |
| NCI-H1650 | Lung | Adenocarcinoma | 10 | Mutant |
| NCI-H1666 | Lung | Adenocarcinoma | 13 | Wild type |
| NCI-H1703 | Lung | Adenocarcinoma, non-small cell lung cancer | 9.1 | Mutant |
| NCI-H1755 | Lung | Adenocarcinoma, non-small cell lung cancer | 7.8 | Mutant |
| NCI-H1781 | Lung | Carcinoma, bronchioalveolar, non-small cell lung cancer | 8.8 | Mutant |
| NCI-H1792 | Lung | Adenocarcinoma | 7 | Mutant |
| NCI-H1793 | Lung | Adenocarcinoma, non-small cell lung cancer | 10 | Mutant |
| NCI-H1838 | Lung | Adenocarcinoma, non-small cell lung cancer | 9.8 | Mutant |
| NCI-H187 | Lung | Carcinoma, classic small cell lung cancer | 15 | Mutant |
| NCI-H1944 | Lung | Adenocarcinoma, non-small cell lung cancer | 7 | Wild type |
| NCI-H1975 | Lung | Adenocarcinoma | 16 | Mutant |
| NCI-H1993 | Lung | Adenocarcinoma, non-small cell lung cancer | 7.7 | Mutant |
| NCI-H2009 | Lung | Adenocarcinoma | 9.9 | Mutant |
| NCI-H2023 | Lung | Adenocarcinoma, non-small cell lung cancer | 5.8 | Mutant |
| NCI-H2029 | Lung | Carcinoma, small cell lung cancer | 5.8 | Mutant |
| NCI-H2030 | Lung | Adenocarcinoma, non-small cell lung cancer | 9.2 | Mutant |
| NCI-H2081 | Lung | Carcinoma, small cell lung cancer | 17 | Wild type |

TABLE 1-continued

CELLO/CACTEL Cell Lines

| Cell Lines | Tissue | Origin | IC50 | TP53 |
|---|---|---|---|---|
| NCI-H209 | Lung | Carcinoma, small cell lung cancer | 11 | Mutant |
| NCI-H2170 | Lung | Carcinoma, squamous cell | 12 | Mutant |
| NCI-H2171 | Lung | Carcinoma, small cell lung cancer | 11 | Mutant |
| NCI-H2227 | Lung | Carcinoma, small cell lung cancer | 16 | Mutant |
| NCI-H2228 | Lung | Adenocarcinoma, non-small cell lung cancer | 9.8 | Mutant |
| NCI-H23 | Lung | Adenocarcinoma, non-small cell lung cancer | 10 | NA |
| NCI-H2347 | Lung | Adenocarcinoma, non-small cell lung cancer | 9 | Wild type |
| NCI-H250 | Lung | Carcinoma, classic small cell lung cancer | 12 | NA |
| NCI-H292 | Lung | Carcinoma, mucoepidermoid pulmonary | 1.6 | Wild type |
| NCI-H345 | Lung | Carcinoma, small cell lung cancer | 17 | Mutant |
| NCI-H358 | Lung, bronchi | Carcinoma, alveola cell | 8.1 | Mutant |
| NCI-H441 | Lung | Adenocarcinoma | 10 | Mutant |
| NCI-H508 | Intestine, large; caecum | Adenocarcinoma, colorectal | 1.2 | Mutant |
| NCI-H520 | Lung | Carcinoma, squamous cell | 17 | Mutant |
| NCI-H526 | Lung | Carcinoma, small cell lung cancer | 16 | Mutant |
| NCI-H661 | Lung | Carcinoma, large cell, neuroendocrine, non-small lung cancer | 11 | Mutant |
| NCI-H69 | Lung | Carcinoma, small cell lung cancer | 15 | Mutant |
| NCI-H716 | Intestine, large; caecum | Adenocarcinoma, colorectal | 13 | Mutant |
| NCI-H748 | Lung | Carcinoma, small cell lung cancer | 16 | Mutant |
| NCI-H82 | Lung | Carcinoma, small cell lung cancer | 4.9 | Wild type |
| NCI-H838 | Lung | Adenocarcinoma, non-small cell lung cancer | 14 | Mutant |
| NCI-N87 | Stomach | Carcinoma, gastric | 12 | Mutant |
| NOMO-1 | Bone marrow | Leukemia, acute myeloid | 6.3 | Mutant |
| NUGC-3 | Stomach | Adenocarcinoma | 9.8 | Mutant |
| OPM-2 | Lymphocyte B | Myeloma, multiple | 13 | Mutant |
| NIH:OVCAR-3 | Ovary | Adenocarcinoma | 17 | Mutant |
| PC-1 | null | null | 1.3 | Wild type |
| PC-10 | Lung | Carcinoma, squamous cell | 14 | Mutant |
| PC-13 | Lung | Adenocarcinoma | 14 | Mutant |
| PC-3 | Prostate | Adenocarcinoma | 9 | Mutant |
| PC-6 | Lung | Carcinoma, small cell lung cancer | 8.2 | Wild type |
| PLC/PRF/5 | Liver | Hepatoma | 7 | Mutant |
| QG-56 | Lung | Carcinoma, non-small cell lung cancer | 10 | Mutant |
| Raji | Lymphocyte B | Lymphoma, Burkitt | 3 | Mutant |
| Ramos | Lymphocyte B | Lymphoma, Burkitt | 8.8 | Wild type |
| RL95-2 | Uterus, endometrium | Carcinoma | 9.3 | Mutant |
| RPMI-8226 | Lymphocyte B, peripheral blood | Myeloma, plasmacytoma | 6.6 | Mutant |
| RT4 | Urinary, bladder | Papilloma, transitional cell | 2.4 | Wild type |
| SCaBER | Urinary, bladder | Carcinoma, squamous cell | 8.5 | Mutant |
| SCC-25 | Tongue | Carcinoma, squamous cell | 9.4 | Mutant |
| SCH | Stomach | Choriocarcinoma | 17 | Mutant |
| SJCRH30 | Muscle | Rhabdomyosarcoma | 16 | Mutant |
| SK-LU-1 | Lung | Adenocarcinoma | 11 | Mutant |
| SK-MES-1 | Lung | Carcinoma, squamous cell | 6 | Mutant |
| SK-N-AS | Brain | Neuroblastoma (Glioma, neuroblastoma) | 13 | Mutant |
| SK-N-DZ | Brain | Neuroblastoma (Glioma, neuroblastoma) | 5.7 | Mutant |
| SK-N-F1 | Brain | Neuroblastoma (Glioma, neuroblastoma) | 17 | Mutant |
| SK-OV-3 | Ovary | Adenocarcinoma | 17 | Mutant |
| SNU-16 | Stomach | Carcinoma, gastric | 10 | Mutant |
| SNU-5 | Stomach | Carcinoma, gastric | 16 | Mutant |
| SU•86•86 | Pancreas | Carcinoma, ductal | 6.7 | Mutant |
| SUM-44PE | Breast | Carcinoma | 3 | Wild type |
| SUM52PE | Breast | Carcinoma | 8.7 | Wild type |
| SW1116 | Intestine, large; colon | Adenocarcinoma, colorectal | 12 | Mutant |
| SW1417 | Intestine, large; colon | Adenocarcinoma, colorectal | 9.9 | Mutant |
| SW1463 | Intestine, large; rectum | Adenocarcinoma, colorectal | 1 | Mutant |
| SW403 | Intestine, large; colon | Adenocarcinoma, colorectal | 6 | Mutant |
| SW480 | Intestine, large; colon | Adenocarcinoma, colorectal | 12 | Mutant |
| SW579 | Thyroid gland | Carcinoma, squamous cell | 16 | Mutant |
| SW620 | Intestine, large; colon | Adenocarcinoma, colorectal | 9.8 | Mutant |
| SW626 | Ovary | Adenocarcinoma | 9.5 | Mutant |
| SW837 | Intestine, large; rectum | Adenocarcinoma | 12 | Mutant |

TABLE 1-continued

CELLO/CACTEL Cell Lines

| Cell Lines | Tissue | Origin | IC50 | TP53 |
|---|---|---|---|---|
| T-47D | Breast, mammary gland | Carcinoma, ductal | 9.9 | Mutant |
| T84 | Intestine, large; colon | Carcinoma, colorectal | 5.3 | Mutant |
| T98G | Brain | Glioblastoma, multiforme | 8.3 | Mutant |
| TCCSUP | Urinary, bladder | Carcinoma, urinary bladder, transitional cell carcinoma | 16 | Mutant |
| TF-1a | Bone marrow | Erythroleukemia OR Leukemia, erythroid | 10 | Mutant |
| THP-1 | Blood | Leukemia, acute monocytic | 9.7 | Mutant |
| TT | Thyroid gland | Carcinoma | 2 | Wild type |
| U-698-M | Tonsil | Lymphoma, lymphoblastic, non-Hodgkin's | 9.8 | Mutant |
| U-937 | Pleura | Lymphoma, histiocytic | 5.2 | Mutant |
| UM-UC-3 | Urinary, bladder | Carcinoma, urinary bladder, transitional cell carcinoma | 15 | Mutant |
| VCaP | Prostate | Carcinoma, prostate | 13 | Mutant |
| WiDr | Intestine, large; colon | Adenocarcinoma, colorectal | 8.9 | Mutant |
| 10C9 | Lymphocyte B | Lymphoma, Non-Hodgkin's | 19 | Mutant |
| 8305C | Thyroid gland | Carcinoma, medullary thyroid | 24 | Mutant |
| A-673 | Muscle | Rhabdomyosarcoma | 18 | Mutant |
| AN3 CA | Uterus, endometrium | Adenocarcinoma | 18 | Mutant |
| AsPC-1 | Pancreas | Adenocarcinoma | 19 | Mutant |
| BFTC-905 | Urinary, bladder | Carcinoma, urinary bladder, transitional cell carcinoma | 19 | Mutant |
| BT-474 | Breast, mammary gland | Carcinoma, ductal | 19 | Mutant |
| BT-483 | Breast, mammary gland | Carcinoma, ductal | 20 | Mutant |
| BxPC-3 | Pancreas | Adenocarcinoma | 18 | Mutant |
| C-33 A | Cervix | Carcinoma, cervix | 18 | Mutant |
| CAMA-1 | Breast, mammary gland | Adenocarcinoma, mammary gland, breast | 22 | Mutant |
| Capan-1 | Pancreas | Adenocarcinoma | 20 | Mutant |
| COLO-704 | Ovary | Carcinoma, ovary | 20 | Wild type |
| EFO-21 | Ovary | Carcinoma, ovary | 31 | Mutant |
| F-36P | Myeloblast | Leukemia, acute myeloid | 23 | Mutant |
| HARA | Lung | Carcinoma, squamous cell | 19 | Mutant |
| HCC1395 | Breast, mammary gland | Carcinoma, primary ductal | 20 | Mutant |
| HDLM-2 | Lymphocyte B | Lymphoma, Hodgkin's disease | 33 | Mutant |
| HeLa S3 | Cervix | Carcinoma, cervix | 20 | Mutant |
| J82 | Urinary, bladder | Carcinoma, urinary bladder, transitional cell carcinoma | 20 | Mutant |
| KARPAS-299 | Blood | Lymphoma | 19 | Mutant |
| Kasumi-1 | Lymphocyte, peripheral blood | Leukemia, acute myeloid | 21 | Mutant |
| KMM-1 | Lymphocyte | Myeloma | 19 | Mutant |
| L-363 | Lymphocyte, peripheral blood | Leukemia, plasma cell | 32 | Mutant |
| MDA-MB-134-VI | Breast, mammary gland | Carcinoma, ductal | 38 | Mutant |
| MDA-MB-157 | Breast, mammary gland | Carcinoma, medula | 20 | Mutant |
| MDA-MB-361 | Breast, mammary gland | Adenocarcinoma, mammary gland, breast | 21 | Mutant |
| MDA-MB-453 | Breast, mammary gland | Carcinoma | 20 | Mutant |
| MFE-280 | Uterus, endometrium | Adenocarcinoma, malignant, endometroid carcinoma | 23 | Mutant |
| MIA PaCa-2 | Pancreas | Carcinoma | 19 | Mutant |
| NCI-H1155 | Lung | Carcinoma, non-small cell lung cancer | 22 | Mutant |
| NCI-H446 | Lung | Carcinoma, small cell lung cancer | 18 | Mutant |
| NCI-H522 | Lung | Adenocarcinoma, non-small cell lung cancer | 22 | Mutant |
| NCI-H596 | Lung | Carcinoma, adenosquamous | 18 | Mutant |
| PANC-1 | Pancreas | Carcinoma, epithelioid | 22 | Mutant |
| SBC-5 | Lung | Carcinoma, small cell lung cancer | 18 | Mutant |
| SCC-15 | Tongue | Carcinoma, squamous cell | 20 | Mutant |
| SK-BR-3 | Pleura | Adenocarcinoma, mammary gland, breast | 21 | Mutant |
| SK-ES-1 | Bone | Sarcoma, Ewing's | 25 | Mutant |
| SKM-1 | Lymphocyte, peripheral blood | Leukemia, acute myeloid | 19 | Mutant |
| SK-MEL-30 | Skin | Melanoma, malignant | 19 | Mutant |
| SW948 | Intestine, large; colon | Adenocarcinoma, colorectal | 19 | Mutant |
| T24 | Urinary, bladder | Carcinoma, urinary bladder, transitional cell carcinoma | 21 | Mutant |
| U-118 MG | Brain | Glioblastoma, astrocytoma | 19 | Mutant |
| U-138 MG | Brain | Glioblastoma | 29 | Mutant |
| U-2197 | Skin, hypodermis; subcutaneous | Histiocytoma, fibrous, malignant | 22 | Mutant |

TABLE 1-continued

CELLO/CACTEL Cell Lines

| Cell Lines | Tissue | Origin | IC50 | TP53 |
|---|---|---|---|---|
| U266B1 | Lymphocyte B | Myeloma, plasmacytoma | 18 | Mutant |
| YAPC | Pancreas | Carcinoma, pancreatic | 18 | Mutant |

CELLO/CACTEL, Oncology/Chugai ACcumulative Tumor EncycLopedia; $IC_{50}$, half maximal inhibitory concentration; NA, Not Available.

Among the 281 cell lines, 210 cell lines show mutations in TP53 after a careful annotation removing low quality calls and germline mutations. Cell lines harboring mutant TP53 are much less sensitive to MDM2 antagonist therapy ($P<2.2\times10^{-16}$), consistent with previously published data. However, two challenges are observed in using TP53 mutation status as a potential predictive biomarker for COMPOUND A. Although not wanting to be limited by theory, first, several TP53 mutant cell lines show sensitive responses to COMPOUND A most likely because they harbor non-functional TP53 mutations, such as 22Rv1, DU145, KMS-12-BM, KMS-26, LCLC-103H, LN-18, MKN-45, NCI-H2122, NCI-H226, PC-9, SW1463.

Some other methods of assaying include but are not limited to a) immunohistochemistry (IHC) analysis, b) western blotting c) immunoprecipitation d) enzyme linked immunosorbant assay (ELISA) e) radioimmunoassy f) Fluorescence activated cell sorting (FACS) g) mass spectrometry, including matrix assisted laser desorpotion/ionisation (MALDI, e.g. MALDI-TOF) and electrospray ionisation mass-spectrometry (ESI-MS).

One approach for assessing potential response to a MDM2 antagonist is to assess whether or not the TP53 gene is mutated. However, this is complicated by the fact that a multitude of mutations can be found in TP53 in cancer. Not all of these mutations will interfere with activity of the p53 protein, further complicating the interpretation of TP53 mutational tests. In addition, there is a range of responses to MDM2 antagonists in wild type TP53 cell lines and patients. Therefore, the ability to predict responsiveness to an MDM2 antagonist from an easily interpretable diagnostic tool is an unmet need in clinical development of MDM2 antagonists. To this end, the development of a gene expression signature that reflects p53 pathway activity provides a means of selecting patients most likely to respond to MDM2 antagonist therapy.

Towards this end, a genome-wide association between baseline mRNA expression and MDM2 antagonist therapy response (IC50) is performed and identified a list of 13 genes with significant associations with P ranging from $2.38\times10^{-47}$ to $9.56\times10^{-23}$ (Table 2).

Functional annotation indicates that the 13 significant genes from the genomewide association, with correlation coefficients ranging from −0.47 to −0.31 (with one positive correlation 0.28), are known regulators in the relevant MDM2-P53 interactions or downstream P53 pathways, including cell cycle arrest and apoptosis. Among them, MDM2 is the number 4 top gene with an over-expression of MDM2 correlating with in vitro sensitivity, consistent with previously published data.

To further construct an mRNA signature, a multivariate logistic regression classifier is built, among the 13 genes, via upward model selection procedure. The mRNA signature is composed of up-regulations of three genes including MDM2, XPC (xeroderma pigmentosum, complementation group C), BBC3 (BCL2 binding component 3) and down-regulation of tumor suppressor gene CDKN2A cyclin-dependent kinase inhibitor 2a.

TABLE 2

Significant gene expression predictors from genomedwide association

| Ensg.id | Gene | Cor | Pvalue | Mean (Sen) | SD (Sen) | Mean (Res) | SD (Res) | FC | Annotation |
|---|---|---|---|---|---|---|---|---|---|
| ENSG00000087088 | BAX | −0.47 | 9.56E-23 | 5.12 | 0.63 | 4.48 | 0.59 | 1.56 | apoptosis |
| ENSG00000185088 | RPS27L | −0.45 | 2.83E-23 | 4.23 | 0.80 | 3.01 | 0.72 | 2.32 | apoptosis |
| ENSG00000131080 | EDA2R | −0.43 | 1.36E-24 | 0.28 | 3.59 | −4.98 | 2.36 | 38.23 | P53-related |
| ENSG00000154767 | XPC | −0.42 | 5.33E-24 | 3.56 | 0.44 | 2.72 | 0.62 | 1.79 | DNA repair |
| ENSG00000134574 | DDB2 | −0.41 | 4.72E-24 | 4.65 | 0.78 | 3.78 | 0.82 | 1.83 | DNA repair |
| ENSG00000161513 | FDXR | −0.41 | 3.59E-24 | 4.13 | 0.95 | 3.00 | 1.15 | 2.20 | P53-related |
| ENSG00000135679 | MDM2 | −0.39 | 1.12E-24 | 4.63 | 0.87 | 3.60 | 0.64 | 2.04 | |
| ENSG00000124762 | CDKN1A | −0.39 | 1.04E-24 | 5.51 | 1.59 | 3.54 | 2.01 | 3.92 | cell cycle arrest |
| ENSG00000170855 | TRIAP1 | −0.38 | 8.10E-25 | 5.53 | 0.49 | 5.04 | 0.49 | 1.40 | apoptosis |
| ENSG00000105327 | BBC3 | −0.34 | 9.26E-26 | 2.05 | 1.18 | 0.65 | 1.41 | 2.64 | apoptosis |
| ENSG00000113328 | CCNG1 | −0.31 | 1.47E-26 | 5.65 | 0.69 | 4.79 | 0.80 | 1.81 | cell cycle arrest |
| ENSG00000120889 | TNFRSF10B | −0.31 | 1.37E-26 | 4.69 | 1.02 | 3.50 | 1.41 | 2.28 | apoptosis |
| ENSG00000147889 | CDKN2A | 0.28 | 2.38E-47 | −1.71 | 3.79 | 1.35 | 4.26 | 0.12 | MDM2-related |

The final signature is capable of distinguishing MDM2 antagonist sensitive cell lines from MDM2 antagonist resistant cell lines with an area (AUC) under the receiver operating characteristic (ROC) curve of 0.93 (95% CI 0.92 to 0.95, Table 3), estimated from a 10-fold cross-validation. Therefore, the MDM2 antagonist sensitive cell lines demonstrate baseline up-regulation of MDM2, XPC, and BBC3 and down-regulation of CDKN2A; whereas the MDM2 antagonist resistant cell lines are characterized by down regulation of MDM2, XPC, and BBC3 and up-regulation of CDKN2A. (See FIG. 2).

TABLE 3

Prediction from various predictive biomarkers

| | CELLO[a] | NO21279[b] |
|---|---|---|
| Score | | |
| AUC | 0.92 | 0.82 |
| Specificity[c] | 0.67 | 0.71 |
| Sensitivity[d] | 0.93 | 1.00 |
| TP53 | | |
| AUC | 0.87 | 0.52 |
| Specificity[e] | 0.95 | 0.19 |
| Sensitivity[f] | 0.80 | 0.86 |
| MDM2 | | |
| AUC | 0.83 | 0.50 |
| Specificity[c] | 0.65 | 0.48 |
| Sensitivity[d] | 0.85 | 0.43 |

[a]Responders defined as IC50 < 1; Non-responders defined as IC50 > 10 in CELLO
[b]Responders defined as CR/MLFS; Non-responders defined as HI/PD in NO21279
[c]Specificity: Proportion of non-responders that have scores or MDM2 expression lower than corresponding Youden Index
[d]Sensitivity: Proportion of responders that have scores or MDM2 expression higher than corresponding Youden Index
[e]Specificity: Proportion of non-responders that have TP53 mutations
[f]Sensitivity: Proportion of responders that have wild type TP53

In addition to the target gene MDM2, the other three genes in the signature are all biologically supported as regulators in the MDM2-p53 interactions or downstream p53 pathways. The XPC gene plays an important role involved in repairing damaged DNA, contributing to damage recognition, open complex formation, and repair protein complex formation. BBC3 mRNA levels are induced by exposure to DNA-damaging agents and by p53, which mediates DNA damage-induced apoptosis. The two gene products of the CDKN2A, p16 and p14ARF, are both linked to major tumor suppressor pathways; especially p14ARF, which inhibits MDM2 function by sequestering it in the nucleolus. To examine the molecular mechanisms underlying the mRNA signature, the mRNA signature score is correlated with mutation status of P53 and key regulatory genes involved in MDM2-P53 interactions and downstream P53 pathways.

Figure 2:
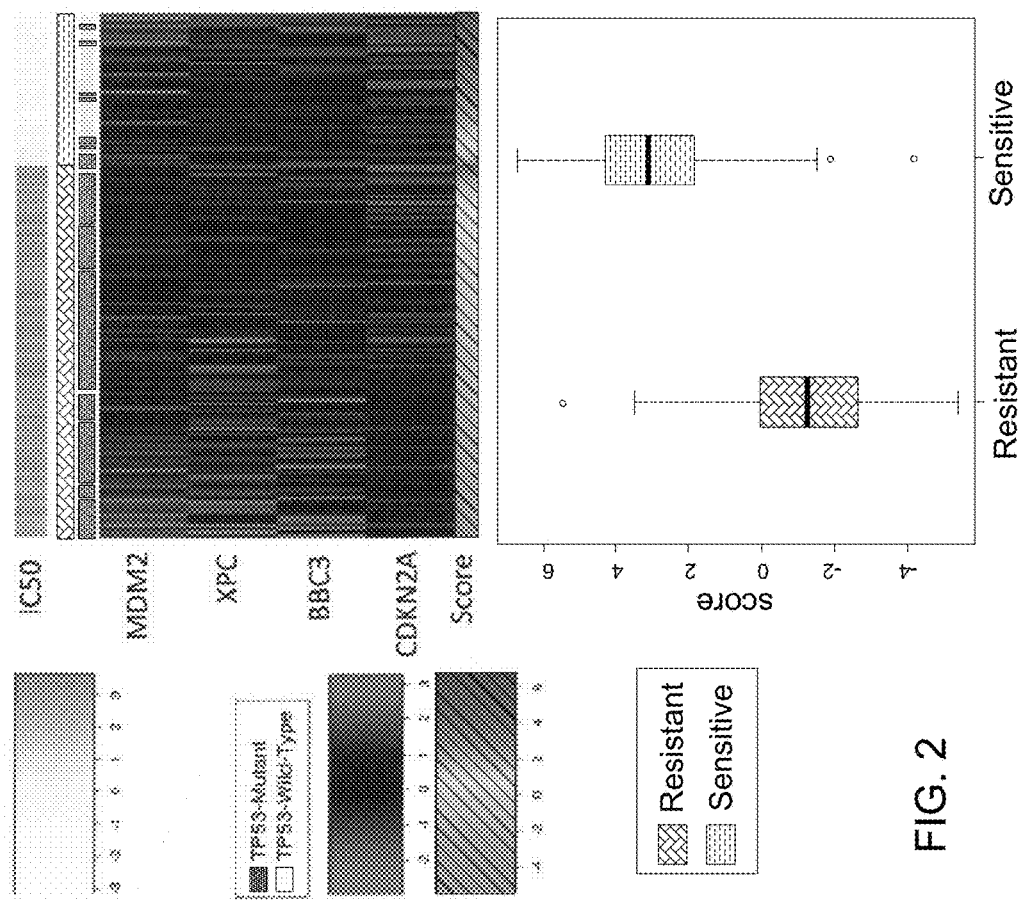
FIG. 2: MDM2 antagonist response mRNA signature in vitro.

As shown in FIG. 2, cell lines with low signature score are more likely to be p53 mutant; whereas cell lines with high signature score are more likely to be p53 wild type (P<2.2× $10^{-16}$). See p53 mutation status for each cell line in Table 4. Furthermore, the majority of resistant cell lines with wild type TP53 but low signature score harbor mutations in key regulatory genes involved in MDM2-P53 interactions and downstream P53 pathways. This indicates that the signature score can serve as a surrogate mRNA-level indicator of MDM2-P53 pathway function.

TABLE 4 p53 mutation status versus signature score

| Cell lines | Tissue | Origin | IC50 | Score | Mutation in TP53 |
|---|---|---|---|---|---|
| 10C9 | Lymphocyte B | Lymphoma, Non-Hodgkin's | 19.0 | −0.8 | Mutant |
| 143B | Bone | Osteosarcoma | 15.0 | 0.2 | Mutant |
| 22Rv1 | Prostate | Carcinoma | 1.0 | 3.0 | Mutant |
| 647-V | Urinary tract, urothelium | Carcinoma, urinary bladder, transitional cell carcinoma (TCC) | 17.0 | −1.6 | Mutant |
| 8305C | Thyroid gland | Carcinoma, medullary thyroid | 24.0 | −3.8 | Mutant |
| A-172 | Brain | Glioblastoma | 0.6 | 1.4 | Wild Type |
| A2058 | Skin | Melanoma | 17.0 | −2.8 | Mutant |
| A-375 | Skin | Melanoma, malignant | 0.3 | 2.8 | Wild Type |
| A549 | Lung | Carcinoma, squamous cell | 0.9 | 2.4 | Wild Type |
| A-673 | Muscle | Rhabdomyosarcoma | 18.0 | 0.9 | Mutant |
| ACHN | Kidney | Adenocarcinoma, renal cell | 0.3 | 4.1 | Wild Type |
| AGS | Stomach | Adenocarcinoma, gastric | 0.1 | 5.4 | Wild Type |
| AN3 CA | Uterus, endometrium | Adenocarcinoma | 18.0 | −1.2 | Mutant |
| ARH-77 | Lymphocyte B, peripheral blood | Leukemia, plasma cell | 17.0 | 0.3 | Mutant |
| AsPC-1 | Pancreas | Adenocarcinoma | 19.0 | −1.3 | Mutant |
| BFTC-905 | Urinary, bladder | Carcinoma, urinary bladder, transitional cell carcinoma (TCC) | 19.0 | −0.7 | Mutant |
| BT-474 | Breast, mammary gland | Carcinoma, ductal | 19.0 | 1.5 | Mutant |
| BT-483 | Breast, mammary gland | Carcinoma, ductal | 20.0 | 1.1 | Mutant |
| BxPC-3 | Pancreas | Adenocarcinoma | 18.0 | −2.2 | Mutant |
| C-33 A | Cervix | Carcinoma, cervix | 18.0 | −0.6 | Mutant |
| Caki-1 | Kidney | Carcinoma, clear cell | 0.4 | 4.5 | Wild Type |
| Calu-1 | Lung | Carcinoma, lung epidermoid OR Carcinoma, epidermoid pulmonary | 14.0 | −3.3 | Wild Type |
| Calu-3 | Lung | Adenocarcinoma | 11.0 | −3.4 | Mutant |
| Calu-6 | Lung | Carcinoma, anaplastic | 17.0 | −0.8 | Mutant |
| CAMA-1 | Breast, mammary gland | Adenocarcinoma, mammary gland, breast | 22.0 | 1.9 | Mutant |
| Capan-1 | Pancreas | Adenocarcinoma | 20.0 | 0.7 | Mutant |
| COLO 201 | Intestine, large; colon | Adenocarcinoma, colorectal | 10.0 | −3.2 | Mutant |
| COLO 320DM | Intestine, large; colon | Adenocarcinoma, colorectal | 12.0 | −4.9 | Mutant |
| COLO-704 | Ovary | Carcinoma, ovary | 20.0 | 0.5 | Wild Type |
| COLO-824 | Breast | Carcinoma | 15.0 | −2.9 | Wild Type |
| D341 Med | Brain, cerebellum | Medulloblastoma | 0.0 | 3.5 | Wild Type |
| DMS 114 | Lung | Carcinoma, classic small cell lung cancer | 10.0 | 1.7 | Mutant |
| DU145 | Prostate | Carcinoma, prostate | 1.0 | −4.1 | Mutant |

TABLE 4-continued p53 mutation status versus signature score

| Cell lines | Tissue | Origin | IC50 | Score | Mutation in TP53 |
|---|---|---|---|---|---|
| EFO-21 | Ovary | Carcinoma, ovary | 31.0 | −2.1 | Mutant |
| F-36P | Myeloblast | Leukemia, acute myeloid | 23.0 | 2.7 | Mutant |
| HARA | Lung | Carcinoma, squamous cell | 19.0 | −5.1 | Mutant |
| HARA-B | Lung | Carcinoma, squamous cell | 10.0 | −4.1 | Mutant |
| HCC1143 | Breast, mammary gland | Carcinoma, primary ductal | 12.0 | 0.4 | Mutant |
| HCC1187 | Breast, mammary gland | Carcinoma, primary ductal | 12.0 | −3.7 | Mutant |
| HCC1395 | Breast, mammary gland | Carcinoma, primary ductal | 20.0 | −1.5 | Mutant |
| HCC1500 | Breast, mammary gland | Carcinoma, primary ductal | 1.0 | 4.8 | Wild Type |
| HCC1569 | Breast, mammary gland | Carcinoma, primary metaplastic | 15.0 | −2.1 | Mutant |
| HCC1806 | Breast, mammary gland | Carcinoma, primary acantholytic squamous cell | 11.0 | −4.2 | Mutant |
| HCC1937 | Breast | Carcinoma, ductal | 15.0 | −1.9 | NA |
| HCC1954 | Breast, mammary gland | Carcinoma, ductal | 12.0 | −4.2 | Mutant |
| HCC38 | Breast, mammary gland | Carcinoma, primary ductal | 12.0 | 0.5 | Mutant |
| HCT116 | Intestine, large; colon | Carcinoma, colorectal | 0.5 | 1.4 | Wild Type |
| HCT-8 | Intestine, large; colon | Adenocarcinoma, colorectal, ileocecal | 16.0 | 3.5 | Wild Type |
| HDLM-2 | Lymphocyte B | Lymphoma, Hodgkin's disease | 33.0 | 0.6 | Mutant |
| HEC-1-A | Uterus, endometrium | Adenocarcinoma | 16.0 | 0.0 | Mutant |
| HEL | Lymphocyte, peripheral blood | Erythroleukemia OR Leukemia, erythroid | 17.0 | 2.3 | Mutant |
| HeLa S3 | Cervix | Carcinoma, cervix | 20.0 | 0.7 | Mutant |
| HepG2 | Liver | Carcinoma, hepatocellular | 0.2 | 2.4 | Wild Type |
| HMCB | Skin | Melanoma | 15.0 | −2.2 | Mutant |
| HPAF-II | Pancreas | Adenocarcinoma | 10.0 | −0.6 | Mutant |
| Hs 38•T | Ovary | Teratoma | 0.7 | −0.4 | Wild Type |
| Hs 766T | Pancreas | Carcinoma | 17.0 | −0.7 | Mutant |
| HT-1080 | Connective tissue | Fibrosarcoma | 0.1 | 6.3 | Wild Type |
| HT-1197 | Urinary, bladder | Carcinoma, urinary bladder, papillary (PAP) | 0.2 | 6.5 | Wild Type |
| HT-1376 | Urinary, bladder | Carcinoma | 16.0 | 1.4 | Mutant |
| HuH-28 | Gall bladder | Carcinoma, bile duct OR Cholangiocarcinoma | 15.0 | −2.0 | Mutant |
| HUP-T4 | Pancreas | Carcinoma, pancreatic | 17.0 | −0.4 | Mutant |
| IM-9 | Lymphocyte B, peripheral blood | Myeloma, multiple | 0.1 | 4.2 | Wild Type |
| IMR-32 | Brain | Neuroblastoma (Glioma, neuroblastoma) | 0.4 | 3.2 | Wild Type |
| J82 | Urinary, bladder | Carcinoma, urinary bladder, transitional cell carcinoma (TCC) | 20.0 | −2.4 | Mutant |
| JIMT-1 | Breast | Carcinoma | 11.0 | −1.4 | Mutant |
| K-562 | Bone marrow | Leukemia, chronic myeloid | 16.0 | 5.5 | Mutant |
| KARPAS-299 | Blood | Lymphoma | 19.0 | 0.1 | Mutant |
| Kasumi-1 | Lymphocyte, peripheral blood | Leukemia, acute myeloid | 21.0 | −2.7 | Mutant |
| KELLY | Brain | Neuroblastoma (Glioma, neuroblastoma) | 15.0 | 0.0 | Mutant |
| KG-1 | Bone marrow | Leukemia | 15.0 | −2.5 | Mutant |
| KMM-1 | Lymphocyte | Myeloma | 19.0 | −0.6 | Mutant |
| KMS-11 | Lymphocyte | Myeloma, multiple | 12.0 | −1.7 | Wild Type |
| KMS-12-BM | Bone marrow | Myeloma, multiple | 0.0 | 1.3 | Mutant |
| KMS-20 | Lymphocyte | Myeloma | 13.0 | 0.0 | Mutant |
| KMS-21BM | Bone marrow | Myeloma, multiple | 0.0 | 3.6 | Wild Type |
| KMS-26 | Lymphocyte | Myeloma | 0.5 | −1.8 | Mutant |
| KYSE-520 | Esophagus; oesophagus | Carcinoma, squamous cell | 10.0 | −3.1 | Mutant |
| L-363 | Lymphocyte, peripheral blood | Leukemia, plasma cell | 32.0 | −0.6 | Mutant |
| LCLC-103H | Lung | Carcinoma, large cell, non-small cell lung cancer | 0.7 | −0.6 | Mutant |
| LN-18 | Brain, temporal lobe | Glioblastoma | 0.7 | 1.1 | Mutant |
| LNCaP clone FGC | NA | NA | 0.2 | 1.8 | Wild Type |
| LS 174T | Intestine, large; colon | Adenocarcinoma, colorectal | 0.6 | 3.6 | Wild Type |
| LS411N | Intestine, large; caecum | Carcinoma, colorectal | 16.0 | 0.9 | Mutant |
| LS513 | Intestine, large; caecum | Carcinoma, colorectal | 0.5 | 4.4 | Wild Type |
| MC/CAR | Lymphocyte B, peripheral blood | Myeloma, plasmacytoma | 0.7 | 3.3 | Wild Type |
| MCF7 | Breast, mammary gland | Adenocarcinoma, mammary gland, breast | 0.8 | 2.9 | Wild Type |
| MDA-MB-134-VI | Breast, mammary gland | Carcinoma, ductal | 38.0 | 0.4 | Mutant |
| MDA-MB-157 | Breast, mammary gland | Carcinoma, medula | 20.0 | −5.4 | Mutant |
| MDA-MB-231 | Breast, mammary gland | Adenocarcinoma | 17.0 | −1.2 | Mutant |
| MDA-MB-361 | Breast, mammary gland | Adenocarcinoma, mammary gland, breast | 21.0 | −0.6 | Mutant |
| MDA-MB-435S | Skin | Melanoma | 12.0 | −3.0 | Mutant |
| MDA-MB-453 | Breast, mammary gland | Carcinoma | 20.0 | −1.4 | Mutant |

TABLE 4-continued p53 mutation status versus signature score

| Cell lines | Tissue | Origin | IC50 | Score | Mutation in TP53 |
|---|---|---|---|---|---|
| MDA-MB-468 | Breast, mammary gland | Adenocarcinoma, mammary gland, breast | 10.0 | −2.8 | Mutant |
| MEG-01 | null | Leukemia, chronic myeloid | 17.0 | −2.8 | Mutant |
| MFE-280 | Uterus, endometrium | Adenocarcinoma, malignant, endometroid carcinoma | 23.0 | −0.9 | Mutant |
| MFM-223 | Breast, mammary gland | Carcinoma, ductal | 17.0 | 2.9 | Mutant |
| MG-63 | Bone | Osteosarcoma | 16.0 | −1.0 | Mutant |
| MIA PaCa-2 | Pancreas | Carcinoma | 19.0 | −0.9 | Mutant |
| MKN-1 | Muscle, smooth, stomach | Carcinoma, squamous cell | 15.0 | −2.9 | Mutant |
| MKN-45 | Stomach | Adenocarcinoma | 0.2 | 4.7 | Mutant |
| MKN-74 | Muscle, smooth, stomach | Carcinoma, gastric | 0.9 | 6.8 | Wild Type |
| MOLM-13 | Blood | Leukemia, acute myeloid | 0.2 | 2.7 | Wild Type |
| MV-4-11 | Blood | Leukemia, acute monocytic | 0.0 | 2.4 | Wild Type |
| NCCIT | Germ cell, gametocyte | Teratocarcinoma | 11.0 | −1.3 | Mutant |
| NCI-H1155 | Lung | Carcinoma, non-small cell lung cancer | 22.0 | −1.6 | Mutant |
| NCI-H1299 | Lung | Carcinoma, non-small cell lung cancer | 15.0 | −2.5 | Mutant |
| NCI-H1437 | Lung | Adenocarcinoma, non-small cell lung cancer | 10.0 | −2.6 | Mutant |
| NCI-H1650 | Lung | Adenocarcinoma | 10.0 | 0.8 | Mutant |
| NCI-H1666 | Lung | Adenocarcinoma | 13.0 | 3.3 | Wild Type |
| NCI-H1793 | Lung | Adenocarcinoma, non-small cell lung cancer | 10.0 | 2.3 | Mutant |
| NCI-H187 | Lung | Carcinoma, classic small cell lung cancer | 15.0 | −1.7 | Mutant |
| NCI-H1975 | Lung | Adenocarcinoma | 16.0 | −2.6 | Mutant |
| NCI-H2081 | Lung | Carcinoma, small cell lung cancer | 17.0 | −2.2 | Wild Type |
| NCI-H209 | Lung | Carcinoma, small cell lung cancer | 11.0 | −1.6 | Mutant |
| NCI-H2122 | Lung | Adenocarcinoma | 0.2 | 2.8 | Mutant |
| NCI-H2170 | Lung | Carcinoma, squamous cell | 12.0 | 0.9 | Mutant |
| NCI-H2171 | Lung | Carcinoma, small cell lung cancer | 11.0 | −1.9 | Mutant |
| NCI-H226 | Lung | Carcinoma, squamous cell | 0.1 | 5.6 | Mutant |
| NCI-H23 | Lung | Adenocarcinoma, non-small cell lung cancer | 10.0 | −0.2 | NA |
| NCI-H28 | null | Mesothelioma | 0.5 | 4.3 | Wild Type |
| NCI-H345 | Lung | Carcinoma, small cell lung cancer | 17.0 | −1.9 | Mutant |
| NCI-H441 | Lung | Adenocarcinoma | 10.0 | −0.4 | Mutant |
| NCI-H446 | Lung | Carcinoma, small cell lung cancer | 18.0 | −0.9 | Mutant |
| NCI-H460 | Lung | Carcinoma | 0.9 | 1.9 | Wild Type |
| NCI-H520 | Lung | Carcinoma, squamous cell | 17.0 | −2.6 | Mutant |
| NCI-H522 | Lung | Adenocarcinoma, non-small cell lung cancer | 22.0 | −1.0 | Mutant |
| NCI-H526 | Lung | Carcinoma, small cell lung cancer | 16.0 | −2.7 | Mutant |
| NCI-H596 | Lung | Carcinoma, adenosquamous | 18.0 | −2.2 | Mutant |
| NCI-H661 | Lung | Carcinoma, large cell, neuroendocrine, non-small lung cancer | 11.0 | −2.0 | Mutant |
| NCI-H69 | Lung | Carcinoma, small cell lung cancer | 15.0 | −0.7 | Mutant |
| NCI-H716 | Intestine, large; caecum | Adenocarcinoma, colorectal | 13.0 | −1.9 | Mutant |
| NCI-H748 | Lung | Carcinoma, small cell lung cancer | 16.0 | 0.3 | Mutant |
| NCI-H838 | Lung | Adenocarcinoma, non-small cell lung cancer | 14.0 | 1.4 | Mutant |
| NCI-H929 | Lymphocyte B, bone marrow | Myeloma, plasmacytoma | 0.3 | 3.1 | Wild Type |
| NCI-N87 | Stomach | Carcinoma, gastric | 12.0 | −2.4 | Mutant |
| NIH:OVCAR-3 | Ovary | Adenocarcinoma | 17.0 | −3.6 | Mutant |
| NKM-1 | Lymphocyte | Leukemia, acute myeloid | 0.3 | 3.3 | Wild Type |
| NUGC-4 | Stomach | Adenocarcinoma | 0.4 | 4.8 | Wild Type |
| OPM-2 | Lymphocyte B | Myeloma, multiple | 13.0 | −2.1 | Mutant |
| PA-1 | Ovary | Carcinoma, ovary | 0.6 | 1.0 | Wild Type |
| PANC-1 | Pancreas | Carcinoma, epithelioid | 22.0 | 0.0 | Mutant |
| PC-10 | Lung | Carcinoma, squamous cell | 14.0 | −1.3 | Mutant |
| PC-13 | Lung | Adenocarcinoma | 14.0 | −1.7 | Mutant |
| PC-9 | Lung | Adenocarcinoma | 0.7 | 0.6 | Mutant |
| QG-56 | Lung | Carcinoma, non-small cell lung cancer | 10.0 | −4.7 | Mutant |
| RKO | Intestine, large; colon | Carcinoma, colorectal | 0.0 | 3.9 | Wild Type |
| RPMI-2650 | Nasal septum | Carcinoma, squamous cell | 0.8 | 3.9 | Wild Type |
| SBC-5 | Lung | Carcinoma, small cell lung cancer | 18.0 | −1.1 | Mutant |
| SCC-15 | Tongue | Carcinoma, squamous cell | 20.0 | −2.9 | Mutant |
| SCH | Stomach | Choriocarcinoma | 17.0 | −0.5 | Mutant |
| SH-SY5Y | Brain | Neuroblastoma (Glioma, neuroblastoma) | 0.8 | 2.6 | Wild Type |
| SJCRH30 | Muscle | Rhabdomyosarcoma | 16.0 | −4.1 | Mutant |
| SK-BR-3 | Pleura | Adenocarcinoma, mammary gland, breast | 21.0 | 0.4 | Mutant |
| SK-ES-1 | Bone | Sarcoma, Ewings | 25.0 | 0.1 | Mutant |
| SK-HEP-1 | Liver | Hepatoma, Hepatocellular carcinoma, HCC | 0.2 | 4.9 | Wild Type |

TABLE 4-continued p53 mutation status versus signature score

| Cell lines | Tissue | Origin | IC50 | Score | Mutation in TP53 |
|---|---|---|---|---|---|
| SK-LU-1 | Lung | Adenocarcinoma | 11.0 | −0.7 | Mutant |
| SKM-1 | Lymphocyte, peripheral blood | Leukemia, acute myeloid | 19.0 | −2.7 | Mutant |
| SK-MEL-1 | Skin | Melanoma, malignant | 0.8 | 0.4 | Wild Type |
| SK-MEL-30 | Skin | Melanoma, malignant | 19.0 | −2.7 | Mutant |
| SK-N-AS | Brain | Neuroblastoma (Glioma, neuroblastoma) | 13.0 | −2.6 | Mutant |
| SK-N-F1 | Brain | Neuroblastoma (Glioma, neuroblastoma) | 17.0 | 0.4 | Mutant |
| SK-N-SH | Brain | Neuroblastoma (Glioma, neuroblastoma) | 0.2 | 2.4 | Wild Type |
| SK-OV-3 | Ovary | Adenocarcinoma | 17.0 | −3.3 | Mutant |
| SNU-1 | Stomach | Carcinoma, gastric | 0.4 | 3.6 | Wild Type |
| SNU-16 | Stomach | Carcinoma, gastric | 10.0 | −1.0 | Mutant |
| SNU-5 | Stomach | Carcinoma, gastric | 16.0 | −0.7 | Mutant |
| SR | Lymphocyte | Lymphoma, large cell | 0.0 | 3.9 | Wild Type |
| SW1116 | Intestine, large; colon | Adenocarcinoma, colorectal | 12.0 | −2.1 | Mutant |
| SW1463 | Intestine, large; rectum | Adenocarcinoma, colorectal | 1.0 | −1.5 | Mutant |
| SW480 | Intestine, large; colon | Adenocarcinoma, colorectal | 12.0 | −0.4 | Mutant |
| SW579 | Thyroid gland | Carcinoma, squamous cell | 16.0 | −0.8 | Mutant |
| SW780 | Urinary, bladder | Carcinoma, urinary bladder, transitional cell carcinoma (TCC) | 1.0 | 5.6 | Wild Type |
| SW837 | Intestine, large; rectum | Adenocarcinoma | 12.0 | −3.3 | Mutant |
| T24 | Urinary, bladder | Carcinoma, urinary bladder, transitional cell carcinoma (TCC) | 21.0 | −2.3 | Mutant |
| TCCSUP | Urinary, bladder | Carcinoma, urinary bladder, transitional cell carcinoma (TCC) | 16.0 | −3.3 | Mutant |
| TF-1a | Bone marrow | Erythroleukemia OR Leukemia, erythroid | 10.0 | −0.8 | Mutant |
| U-118 MG | Brain | Glioblastoma, astrocytoma | 19.0 | 0.4 | Mutant |
| U-138 MG | Brain | Glioblastoma | 29.0 | −1.6 | Mutant |
| U-2197 | Skin, hypodermis; subcutaneous | Histiocytoma, fibrous, malignant | 22.0 | −2.8 | Mutant |
| U266B1 | Lymphocyte B | Myeloma, plasmacytoma | 18.0 | 0.7 | Mutant |
| U-87 MG | Brain | Glioblastoma | 0.2 | 3.1 | Wild Type |
| UM-UC-3 | Urinary, bladder | Carcinoma, urinary bladder, transitional cell carcinoma (TCC) | 15.0 | −0.3 | Mutant |
| VCaP | Prostate | Carcinoma, prostate | 13.0 | −0.4 | Mutant |
| WERI-Rb-1 | Eye, retina | Retinoblastoma | 0.7 | 2.2 | Wild Type |
| Y79 | Eye, retina | Retinoblastoma | 0.6 | 4.9 | Wild Type |
| YAPC | Pancreas | Carcinoma, pancreatic | 18.0 | −1.5 | Mutant |
| ZR-75-1 | Breast, mammary gland | Carcinoma, ductal | 0.1 | 2.2 | Wild Type |

To examine the specific prediction power of the mRNA signature score across the studied tumor types, and to make sure the prediction from the signature score is not confounded by tumor lineage, the signature score within each available tumor type in CELLO is examined.

TABLE 5

Correlation between the mRNA siganture score and mutation status of key regulatory genes invovled in MDM2-p53 interatctions and downstream p53 pathways

| pathway | gene | proportion of mutant lines in resistant lines | propportion of mutant lines in sensitive lines | pvalue |
|---|---|---|---|---|
| apoptosis | ACIN1 | 68% | 58% | 1.32E−01 |
| apoptosis | TP73 | 5% | 0% | 1.33E−01 |
| apoptosis | SPTAN1 | 10% | 4% | 1.45E−01 |
| apoptosis | CASP6 | 4% | 0% | 1.77E−01 |
| apoptosis | IGFBP3 | 4% | 0% | 1.77E−01 |
| apoptosis | RFWD2 | 4% | 0% | 1.77E−01 |
| apoptosis | TP53INP1 | 67% | 58% | 1.80E−01 |
| apoptosis | AKT1 | 3% | 0% | 2.37E−01 |
| apoptosis | TP53I3 | 3% | 0% | 2.37E−01 |
| apoptosis | PTEN | 10% | 6% | 2.70E−01 |
| apoptosis | CASP7 | 2% | 0% | 3.24E−01 |
| apoptosis | NAIP | 2% | 0% | 3.24E−01 |

| | | mean score for mutant lines | mean score for wildtype lines | pvalue |
|---|---|---|---|---|
| apotosis | | −0.03 | 0.14 | 0.58 |
| cell cycle arrest | CDKN2A | 5% | 0% | 1.01E−01 |
| cell cycle arrest | RB1 | 14% | 6% | 1.01E−01 |
| cell cycle arrest | CCNB3 | 8% | 2% | 1.30E−01 |
| cell cycle arrest | CCNE1 | 2% | 0% | 3.24E−01 |
| cell cycle arrest | | −0.97 | 0.24 | 1.00E−02 |

To access the signature robustness measured under various technology platforms, the signature snRNA expressions and the composite score between RNA-seq qualification and microarray quantification is examined. The mRNA signature demonstrated concordance and robustness when measured indifferent tissues and with different technology platforms. The mRNA signature score showed consistence in blood samples and bone marrow aspirate for the same patient at baseline (Spearman correlation coefficient 0·50 [p=0·016]). Therefore, the baseline bone marrow-signature scores were also significantly correlated with patients' clinical responses and pharmacodynamic responses (MDM2 expression change) with Spearman correlation coefficients of 0·46 (p=0·052) and 0·42 (p=0·069), respectively. Furthermore, a high level of concordance between the MDM2 expressions of the 28 patients measured under the two platforms, microarray and quantitative RT-PCR, in blood samples was also observed (Spearman correlation coefficient 0·5

[p=0·019]). These results highlight the possibility of translating the signature into a reproducible, easy-to-standardize predictive assay (see also Table 8, Example 3).

The performance of the MDM2 antagonist predictive mRNA response signature is tested in the clinical setting with specimens from the NO21279 leukemia trial (FIG. 1). 28 AML patients treated at the MTD are enrolled and completed pretreatment and C1D10 (cycle 1, day 10) sampling. Patients are composed of 18 men and 10 women with a median age 59 years (Table 6). The clinical endpoint in NO21279 was divided into 4 categories: Complete Response (CR), Morphologic Leukemia-Free State (MLFS), Hematologic Improvement (HI), and Progressive Disease (PD). Blood leukemia samples and bone marrow biopsy samples were collected at baseline screening, after a single dose (cycle 1 day 2, C1D2) and on last day of dosing (cycle 1, day 10, C1D10) and isolated via MACS® separation[11]. The early pharmacodynamic effect of MDM2 antagonism in blood leukemia samples was assessed by measuring MDM2 RT PCR change between baseline and C1D10. Global gene expression profiles were generated for the peripheral blood leukemia cells and bone marrow biopsy samples obtained at baseline, C1D2 and C1D10.

The biomarker panel measurement procedures have been previously reported[11]. Analysis of TP53 mutations was done by Caris Life Sciences (Irving, Tex., USA) using the PCR-based and microarray-based AmpliChip TP53 test (in development, Roche Molecular Systems, Pleasanton, Calif., USA). This test reports single nucleotide substitutions or deletions in exons 2-11 and their splice sites[11, 14]. MDM2 mRNA concentrations were assessed at Roche Molecular Systems by quantitative real-time PCR with 50 ng total RNA from MACs isolated leukemia cells from blood. TaqMan (Invitrogen, Carlsbad, Calif., USA) probes were designed to detect MDM2 mRNA and the reference mRNA, beta-glucuronidase, simultaneously using two different fluorescent reporters. Gene expression profiles were generated using Affymetrix U133 Plus 2.0 microarrays. Probset ID's for the each of the four genes on said U133 Plus 2.0 microarray are: 209375_s_at (for XPC); 205386_s_at and 211832_s_at (MDM2); 211692_s_at (BBC3); 207039_at and 211156_at (CDKN2A). The "mRNA expression level" for one of the 4 genes according to the present invention is the accumulation of all counts falling into the range of exons of a gene (e.g. MDM2). If there are two probesets for one gene, their average (on log 2 scale) is used. The predictive patient signature score according to the present invention is then calculated using the the following equation: patient signature score=$G_{MDM2}+G_{XPC}+G_{BBC3}-G_{CDKN2A}$. G in the formula stands for log 2 transformed mRNA expression levels as obtained from patient samples, for example blood leukemia or bone marrow biopsy samples. For example, for the patient data reported in Table 9 (Example 5), G is log 2 of the mRNA probeset expression of the relevant gene as measured with Affymetrix U133 Plus 2.0 microarrays. The correlations between signature score and clinical response (progressive disease<hematologic improvement<morphologic leukaemia-free response<complete response) or the pharmacodynamic response (MDM2 expression change) was examined using Spearman correlation coefficients. The median change from baseline of MDM2 expression was examined using the Wilcoxon signed rank test against a median change of 0. An optimal signature-score cutoff using the Youden index of the ROC curve was chosen to classify patients into high- and low-score groups. All statistical analyses were performed in R 2•14•1. According to these data, a patient signature score of about 15 is predictive for the patient's likely response to treatment with an MDM2 inhibitor. In a preferred embodiment, a patient signature score above 15.4 is predictive for the patient's likely response to treatment with an MDM2 inhibitor.

Based on tumor specimen assessments, 23 of 28 patients have wild-type TP53 and 5 patients have TP53 mutations. On day 1, median values for the area under the curve of 24 hour (AUC0-24 h) for RG7112 are 190,315 ng*h/mL (IQR: 119,032-242,857 ng*h/mL) among the 28 studied patients. Clinical responses in the 28 patients include 3 CR, 4 MLFS, 6 HI and 15 PD. Median MDM2 mRNA expression in samples from C1D10 is increased by 2.46 times (IQR: 1.62-4.59) over baseline, demonstrating a pharmacodynamic biomarker response resulting from p53 activation of MDM2 transcription. Drug exposure significantly correlates with patients' clinical responses (p=0.002). 8 of 15 PD patients have insufficient exposures, defined as AUC0-24 h less than 150,000 ng*h/mL; whereas only 1 patient has insufficient exposures in the other three categories.

TABLE 6

Summary of patient characteristics

| Trial | NO21279 | NO21280 | NP22890 |
|---|---|---|---|
| tumor type | AML | advanced malignancies | liposarcoma |
| no. of patients | 28 | 22 | 14 |
| Mean Age (SD) | 53.3 (17.6) | 57.1 (15.0) | 61.4 (14.5) |
| No. of Female (%) | 10 (35) | 11 (50) | 6 (43) |
| No. of patients with P53 mutation | 5 | 0 | 2 |

The identified 4-gene signature score is calculated for each of the 28 patients with AML by taking the summation of MDM2, BBC3, XPC, subtracting CDKN2A expression levels at baseline. There is a significant correlation between the signature scores and patients' clinical responses (PD<HI<MLFS<CR) to MDM2 antagonist therapy (Spearman correlation coefficient 0.58, P=6.6×10$^{-4}$). The signature scores also significantly correlate with patients' pharmacodynamic biomarker responses as measured by MDM2 mRNA change from baseline to C1D10 (Spearman correlation coefficient 0.41, P=0.02). The correlation between the signature scores and patients' clinical responses is further enhanced for the subset of 15 patients with sufficiently high exposures, defined as patients with $AUC_{0-24\ h}$ higher than 150,000 ng*h/mL (Spearman correlation coefficient 0.64, P=5.2×10$^{-3}$).

This 4 gene signature panel is capable of distinguishing AML patients in response categories following treatment with MDM2 inhibitors in the following manner: CR/MLFS patients from PD/Hl patients with an AUC of the ROC curve of 0.82, and distinguishing CR/MLFS/HI patients from PD patients with an AUC of 0.83. In contrast, MDM2 mRNA expression as a single biomarker could only distinguish CR/MLFS patients from PD/HI patients with an AUC of 0.51, and distinguish CR/MLFS/Hl patients from PD patients with an AUC of 0.61. Using a cut-off point of the signature score 15, patients are classified into likely-responder group and likely-non-responder group at baseline prior to MDM2 antagonist therapy with 100% sensitivity and 71% specificity. Therefore, the signature panel has significant potential to be used as a companion predictive biomarker of MDM2 antagonist therapy to select a subset of AML patients who are most likely to respond; and avoid exposing the AML patients who are less likely to respond.

Therefore, in one embodiment, the present invention provides an in vitro method of identifying a patient suffering from cancer as likely to respond to a therapy comprising an MDM2 inhibitor, the method comprising,
a) measuring the mRNA expression level of MDM2, XPC, BBC3 and CDKN2A in a sample obtained from that patient prior to treatment;
b) applying the expression levels obtained in a) to a mathematical equation in order to calculate the patient's signature score;
c) comparing said patient's signature score obtained from h) to a reference level; and
c) identifying said patient as more likely to respond to the therapy comprising said MDM2 inhibitor when the patients's signature score is above said reference level.

In one embodiment, the patient signature score above the reference level indicates a patient's high likelihood to respond to treatment with an MDM2 inhibitor, whereas a signature score below said level indicates that said patient is less likely to respond to that treatment. In one embodiment, the sample obtained in a) is blood leukemia sample, or a bone marrow biopsy sample.

In one embodiment, the mRNA expression levels in a) were generated using Affymetrix U133 Plus 2.0 microarrays. In another embodiment, the mRNA expression levels in a) were generated using RNA sequencing (RNA-seq), for example Next Generation Sequencing (NGS) technology.

In another embodiment, the patient's signature score in b) is calculated from the sum of log 2-transformed mRNA expression levels measured at baseline (i.e. prior to treatment), multiplied by the observed direction in-vitro, defined as signature score=$G_{MDM2}+G_{XPC}+G_{BBC3}-G_{CDKN2A}$. Within this embodiment, mRNA expression levels at baseline are measured by microarray measurements, preferably by using GeneChip Human Genome U133 Plus 2.0 Array. Also, within this embodiment, mRNA expression levels at baseline may be measured by RNA sequencing In another embodiment, the reference level for the patient signature score is 15. In a preferred embodiment, the reference level for the patient signature score is 15.4.

In another embodiment the cancer is a haematological tumor, preferably AML.

In another embodiment, the cancer is a solid tumor, such as for example lung, prostate, colon, head, neck, or pancreatic cancer or sarcoma or melanoma.

In one embodiment, the MDM2 inhibitor is a compound according to formula I, II, III, or combinations thereof.

In another embodiment, the MDM2 inhibitor is the compound A (RG7112) as defined herein.

In yet another embodiment, the MDM2 inhibitor is the compound 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, of the formula

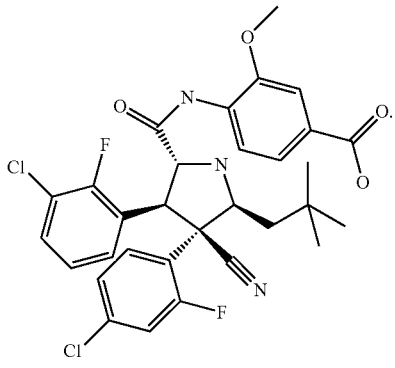

Molecular Weight = 616.4973
Molecular Formula = C31H29Cl2F2N3O4

In yet another embodiment, the MDM2 inhibitor is the compound 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2000).

In yet another embodiment, the MDM2 inhibitor is the compound 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2200).

In still another embodiment, there is provided the use of a gene expression (mRNA) signature to predict a patients response to treatment with an MDM2 inhibitor (antagonist). Within this embodiment, the "gene expression signature" is a 4-gene mRNA signature consisting of MDM2, XPC, and BBC3 elevated expression as well as low expression of CDKN2A when measured at baseline, i.e. prior to treatment with an MDM2 inhibitor (antagonist).

The signature score measurements also correlate with patient's pharmacodynamic biomarker responses (MDM2 expression change). The data presented in Example 5 demonstrate that the 4 mRNA signature score according to the present invention is also a pharmacodynamic biomarker for monitoring efficacy of cancer treatment comprising an MDM2 inhibitor. Therefore, in another embodiment, there is provided an in vitro method for monitoring efficacy of therapy comprising an MDM2 inhibitor, as defined above, in a patient suffering from cancer, the method comprising
a) measuring the mRNA expression level of MDM2, XPC, BBC3 and CDKN2A in a sample obtained from that patient prior to treatment;
b) applying the expression levels obtained in a) to a mathematical equation in order to calculate the patient's signature score prior to treatment;
c) repeating step a) and b) after start of treatment with said MDM2 inhibitor; and
d) comparing the signature scores obtained after start of treatment with those obtained prior to treatment, whereas higher signature scores after treatment indicate a response of the patient to the treatment, and thus a recommendation to continue the treatment.

Within this embodiment, an MDM2 inhibitor is as defined above. The cancer is a solid tumor or AML. The sample obtained in a) is blood leukemia sample, or a bone marrow biopsy sample. Also within this embodiment, the signature score during treatment is preferably obtained at day 10 after the start of treatment, i.e. after the initial administration of an MDM2 inhibitor. The difference in the signature score at day 10 subsequent to initial dosing of an MDM2 inhibitor is at least 1.20 times the score measured at baseline, i.e. prior to treatment. In a preferred embodiment, a signature score at day 10 after initial dosing of an MDM2 inhibitor of about 1.23 to about 1.26 times the score measured prior to treatment, indicates that the patient responds to treatment and that the treatment should be continued.

A compound according to formula I, II, III, or combinations thereof, or pharmaceutically acceptable derivatives thereof may be used for the prophylactic or especially therapeutic treatment of the human or animal body (subject) (patient), in particular for treating a neoplastic disease (cancer). Examples of such cancers include, but are not limited to, epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell tumours, immunoproliferative diseases, leukemias, miscellaneous myeloproliferative disorders, lymphoproliferative disorders and myelodysplastic syndromes.

Particularly preferably, the disease according to the invention is a neoplastic disease, cancer, and more particularly AML.

Examples of cancers in terms of the organs and parts of the body affected include, but are not limited to, the breast, cervix, ovaries, colon, rectum, (including colon and rectum i.e. colorectal cancer), lung, (including small cell lung cancer, non-small cell lung cancer, large cell lung cancer and mesothelioma), bone, endocrine system, adrenal gland, thymus, liver, stomach, intestine, (including gastric cancer), pancreas, bone marrow, hematological malignancies, (such as lymphoma, leukemia, myeloma or lymphoid malignancies), bladder, urinary tract, kidneys, skin, thyroid, brain, head, neck, prostate and testis. Preferably the cancer is selected from the group consisting of breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma and sarcomas. Especially preferably the cancer is selected from the group consisting of breast cancer, cervical cancer, ovarian cancer, colorectal cancer, melanoma and lung cancer. More especially preferably the cancer is selected from the group consisting of lung cancer, melanoma, ovarian cancer and colorectal cancer. In another preferred embodiment, for the case when the resistance predicted is acquired resistance, the cancer is lung cancer or ovarian cancer. In yet another preferred embodiment, for the case where the resistance predicted is inherent resistance, the cancer is selected from the group consisting of colorectal cancer, lung cancer or melanoma.

Method of Treatment

The invention also involves a method of treatment, wherein the activity level of a sample from a patient for sensitivity is first established relative to a standard level or set of standard levels or pre-treatment initiation levels and then a compound of general formula I, II, III, or a pharmaceutically acceptable derivative thereof as defined above, is administered. The compound of formula I, II or III or a pharmaceutically acceptable derivative thereof may be administered in a pharmaceutical composition, as is well known to a person skilled in the art. Compositions for administration, such as nasal, buccal, rectal or, especially, oral administration, and for parenteral administration, such as intravenous, intramuscular or subcutaneous administration, to warm-blooded animals, especially humans, are especially preferred. More particularly, compositions for intravenous administration are preferred.

A compound of general formula I, II or III or a pharmaceutically acceptable derivative thereof can be administered alone or in combination with one or more other therapeutic agents. Possible combination therapy may take the form of fixed combinations, or the administration of a compound of the invention and one or more other therapeutic agents which are staggered or given independently of one another, or the combined administration of fixed combinations and one or more other therapeutic agents.

A compound of general formal I, II or III or a pharmaceutically acceptable derivative thereof can, besides or in addition, be administered especially for tumour therapy in combination with chemotherapy (cytotoxic therapy), targeted therapy, endocrine therapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumour regression, or even chemopreventive therapy for example in patients at risk.

Kit and Device

In one aspect the invention relates to a kit and in another aspect to a device for predicting the response, preferably of a cancer in a subject (or patient), to a compound of general formula I, II, III or a pharmaceutically acceptable derivative thereof as defined, comprising reagents necessary for measuring the MDM2 gene.

The kit and device may also preferably comprise a comparator module which comprises a standard value or set of standard values to which the level of MDM2 in the sample is compared. In a preferred embodiment, the comparator module is included in instructions for use of the kit. IN another preferred embodiment the comparator module is in the form a display device, for example a strip of colour or numerically coded material which is designed to be placed next to the readout of the sample measurement to indicate resistance levels. The standard value or set of standard values may be determined as described above.

The following examples are illustrative of the invention and not limitative thereof.

Example 1

RNA Sequencing of CELLO Cell Lines

RNA sequencing (RNA-seq) by Next Generation Sequencing (NGS) technology is an accurate and sensitive approach to measure gene expression, with the additional power to detect alternative splicing, allele specific expression, non-coding RNA, and various forms of mutations (SNPs, indels, gene fusions). The NGS Illumina HiSeq machine generates raw base calls in reads of 50 or 100 bp length, which are subjected to several data analysis steps. The RNA-seq is conducted at 40 to 50 million reads per sample. This number provides relatively high sensitivity to detect low-expressed genes while allowing for cost-effective multiplexing of samples. RNA is prepared by standard kits and RNA libraries by polyA TruSeq Illumina kits. 100 ng of mRNA per cell line is used for each RNA-seq reaction. A number of quality control procedures are applied to the RNA-seq data for each sample. The Illumina HiSeq software reports the total number of clusters (DNA fragments) loaded in each lane, percent passing sequencing quality filters (which identifies errors due to overloading and sequencing chemistry), a phred quality score for each base of each sequence read, overall average phred scores for each sequencing cycle, and overall percent error (based on alignment to the reference genome). For each RNA-seq sample, the percentage of reads that contain mitochondrial and ribosomal RNA is calculated. The FASTQC package is used to provide additional QC metrics (base distribution, sequence duplication, overrepresented sequences, and enriched kmers) and a graphical summary. Finally, the Picard toolkit that provides additional RNA-seq metrics including an estimate of 3" bias is used (caused by the use of poly-A capture or priming for cDNA synthesis in sample preparation), the percentage of reads mapping to exons, introns and intergenic regions.

RNA Sequencing Pre-Processing Methods

The pipeline for gene expression analysis of RNA-seq data consists of the following steps: First align reads to the protein coding human transcriptome as defined by Ensembl (version 60) in order to identify reads mapping to protein coding RNA (including known splice junctions). In a second step, all reads that do not map to the transcriptome in the first step are subsequently mapped to the human genome. For both mapping steps we use Novolign with standard parameters. After the mapping step, in-house software is used to summarize and count reads mapping to a gene (again defined by Ensembl version 60) and compute RPKM values (as proposed by Mortazavi et al.) based on those raw read counts. Genes with expression levels smaller than RPKM=1 across all cell lines (this is roughly equivalent to an expression level less than one RNA copy per cell) were removed from the dataset.

Example 2

Exom-Sequencing of CELLO Cell Lines

Genomic DNA was extracted from the cells with DNeasy® Blood & Tissue Kit (Qiagen), followed by exome capture using the Roche NimbleGen SeqCap EZ Human Exome Library v2.0 (HG19). The captured libraries were then sequenced on the Illumina HiSeq2000 platform according to the manufacturer's instructions. The resultant paired ends 100 bp reads were trimmed back to 87 bases to minimize low quality sequence stretches at the 3-prime end. Sequence reads were mapped to the HG19 human reference genome (downloaded from http://genome.ucsc.edu) using the Novoalign short read aligner version 2•07•18.[22] Alignments were subsequently sorted with samtools version 0•1•16 and PCR duplicate removal was done with the Picard MarkDuplicates program.[24,25] Read quality scores were recalibrated with Genome Analysis Toolkit (GATK) TableRecalibration walker.[26] Local realignments were then performed with samtools calmd method to better discover SNVs around insertion/deletion (indel) regions. SNVs were called using GATK Unified Genotyper version 1•4, while indel calling was performed using Dindel version 1•01.[26] Variants were further annotated using functional annotation and prediction tools including GATK GenomicAnnotator, snpEff (version 2•3•02), SIFT, and PolyPhen2.[27-29] PolyPhen2 reports the amino acid mutation score in the range of 0-1 with 0•851-1•0 for probably damaging mutations, 0•201-0•850 for possibly damaging mutations, and 0-0•2 for benign mutations. The genotypes were also reported, along with the genotype quality value (Phred score). Based on the genotype calls, homozygous alternate or heterozygosity was then determined. The FASTQC package was used to provide additional QC metrics relating to read quality, sequence duplication, overrepresented sequences, etc.[30] Single-nucleotide variants (SNV s) for low coverage≤10 and a qScore<4 were filtered. This was found to be a meaningful cutoff as mutations below a qScore of four were not reproducible in a technical replicate. Further, the annotation of snpEff was used to focus on mutations that alter amino acid sequences of proteins.

COMPOUND A In Vitro Assay 281 cells are treated with MDM2 antagonists and the IC50 (therapy response) is generated. The cell lines span a broad range of tumor cell types of derivation.

Among the 281 cell lines evaluated, 210 cell lines show mutations in TP53 after a careful annotation removing low quality calls and germline mutations. Among the 7 AML cell lines tested, 5 showed mutations in TP53. Cell lines harboring mutant TP53 are much less sensitive to MDM2 antagonist therapy ($P<2.2\times10^{-16}$), consistent with previously published data. The genome-wide association between baseline mRNA expression and MDM2 antagonist therapy response (IC50) identify a list of 13 genes with significant associations with P-values ranging from $2.38\times10^{-47}$ to $9.56\times10^{-23}$ (Table 2). Functional annotation indicated that the 13 significant genes from the genome-wide association, with correlation coefficients ranging from −0.47 to −0.31 (with one positive correlation 0.28), are known regulators in the relevant MDM2-P53 interactions or downstream P53 pathways, including cell cycle arrest and apoptosis (Table 2). Among them, MDM2 has the $4^{th}$ highest gene with an over-expression of MDM2 correlating with in vitro sensitivity, consistent with previously published data.

A multivariate logistic regression classifier is identified, which contains up-regulations of three genes including MDM2, XPC (xeroderma pigmentosum, complementation group C), BBC3 (BCL2 binding component 3) and down-regulation of tumor suppressor gene CDKN2A (cyclin-dependent kinase inhibitor 2A) (Table 7). The final signature is capable of distinguishing MDM2 antagonist sensitive cell lines from MDM2 antagonist resistant cell lines with AUC of 0.93 (95% CI 0.92 to 0.95). Therefore, the MDM2 antagonist sensitive cell lines demonstrate baseline up-regulation of MDM2, XPC, and BBC3 and down-regulation of CDKN2A; whereas the MDM2 antagonist resistant cell lines are characterized by down-regulation of MDM2, XPC, and BBC3 and up-regulation of CDKN2A (FIG. 2).

In addition to the target gene MDM2, the other three genes in the signature are all biologically supported as regulators in the MDM2-p53 interactions or downstream p53 pathways. The XPC gene plays an important role involved in repairing damaged DNA, contributing to damage recognition, open complex formation, and repair protein complex formation. BBC3, also known as p53 upregulated modulator of apoptosis (PUMA), were induced by exposure to DNA-damaging agents and by p53, which mediates DNA damage-induced apoptosis. The two gene products of the CDKN2A, p16 and p14ARF, are both linked to major tumor suppressor pathways; especially p14ARF, which inhibits MDM2 function by sequestering it in the nucleolus. To examine the molecular mechanisms underlying the mRNA signature, we further correlate the mRNA signature score with mutation status of p53 and key regulatory genes involved in MDM2-p53 interactions and downstream p53 pathways (Table 5). As shown in FIG. 2, cell lines with low signature score were more likely to be p53 mutant; whereas cell lines with high signature score are more likely to be p53 wild type ($P<2.2\times10^{-16}$). Furthermore, we identified that the majority of resistant cell lines with wild type TP53 but low signature score harbor mutations in key regulatory genes involved in MDM2-p53 interactions and downstream p53 pathway. These evidences indicated that the signature score can potentially serve as a surrogate mRNA-level indicator of MDM2-P53 pathway function.

To examine the specific prediction power of the mRNA signature score across the studied tumor types, and to make sure the prediction from the signature score is not confounded by tumor lineage, the signature score within each available tumor type in CELLO (Table 7, 7a) is examined. The predictive power of the signature score is preserved in the AML cell lines.

TABLE 7

Tumor type specific correlation

| Tissue | Number | % Sen | % Res | Mean(Sen) | SD(Sen) | Mean(Res) | SD(Res) | Cor | Pvalue |
|---|---|---|---|---|---|---|---|---|---|
| Bone marrow | 5 | 40.0 | 60.0 | 2.5 | 1.6 | 0.7 | 4.2 | 0.1 | 0.0 |
| Brain | 10 | 50.0 | 50.0 | 2.6 | 0.7 | −0.7 | 1.3 | −0.8 | 0.0 |
| Breast, mammary gland | 20 | 15.0 | 85.0 | 3.3 | 1.3 | −1.1 | 2.4 | −0.1 | 0.0 |
| Intestine, large; colon | 8 | 37.5 | 62.5 | 3.0 | 1.4 | −1.4 | 3.2 | −0.5 | 0.0 |
| Lung | 41 | 14.6 | 85.4 | 2.1 | 2.1 | −1.3 | 1.9 | −0.5 | 0.0 |
| Lymphocyte | 6 | 50.0 | 50.0 | 1.8 | 3.1 | −0.8 | 0.9 | −0.5 | 0.0 |
| Ovary | 6 | 33.3 | 66.7 | 0.3 | 0.9 | −2.1 | 1.9 | −0.3 | 0.0 |
| Pancreas | 9 | 0.0 | 100.0 | NA | NA | −0.8 | 0.9 | 0.2 | 0.0 |
| Skin | 6 | 33.3 | 66.7 | 1.6 | 1.7 | −2.7 | 0.3 | −0.6 | 0.0 |
| Stomach | 8 | 50.0 | 50.0 | 4.6 | 0.8 | −1.2 | 0.8 | −0.7 | 0.0 |
| Urinary, bladder | 8 | 25.0 | 75.0 | 6.0 | 0.6 | −1.3 | 1.7 | −0.8 | 0.0 |

TABLE 7a

Tumour type specific correlations between mRNA signature score and $IC_{50}$s

| Tissue | Number (N) | N (sensitive) | N (resistant) | Spearman correlation of $IC_{50}$ and mRNA signature score | p value |
|---|---|---|---|---|---|
| Adenocarcinoma | 21 | 4 | 17 | −0·5 | 2·56E−04 |
| Adenocarcinoma, colorectal | 7 | 2 | 5 | −0·4 | 7·74E−03 |
| Carcinoma | 8 | 2 | 6 | −0·5 | 8·40E−03 |
| Carcinoma, gastric | 5 | 2 | 3 | −0·6 | 2·26E−02 |
| Carcinoma, primary ductal | 5 | 1 | 4 | −0·7 | 1·99E−02 |
| Carcinoma, squamous cell | 12 | 3 | 9 | −0·6 | 3·36E−03 |
| Carcinoma, urinary bladder, transitional cell carcinoma (TCC) | 7 | 1 | 6 | −0·6 | 1·23E−02 |
| Leukaemia, acute myeloid | 5 | 2 | 3 | −0·2 | 1·13E−02 |
| Myeloma, multiple | 5 | 3 | 2 | −0·7 | 2·36E−02 |
| Neuroblastoma (Glioma, neuroblastoma) | 6 | 3 | 3 | −0·6 | 1·71E−02 |

Example 3

In Vitro Assay Gene Expression Analysis Methods

Messenger RNA (mRNA) expression levels at baseline, prior to MDM2 antagonist therapy, are obtained via RNA sequencing (RNA-seq) and microarray measurement using GeneChip Human Genome U133 Plus 2.0 Array. Gene expression analysis of RNA-seq data is summarized here. First, the sequence reads are mapped to the reference human genome and to an additional database of splice junction fragments derived from known exon locations on the reference genome (Cufflinks software). These mapped reads are then combined to create discrete counts of reads (or sequenced bases) per gene. These gene expression counts are then normalized to equalize the total amount of RNA counts for each sample and corrected for gene/transcript length (RPKM). All genes with expression values less than RPKM=1 in all cell lines are removed (this is roughly equivalent to an expression level less than one copy of an RNA molecule per cell). Next, normalized gene counts are statistically tested to identify differentially expressed genes between responder cell lines and non-responder cell lines using statistical methods that find differentially expressed (DE) genes with negative binomial models. The negative binomial model implemented is the DEseq software. 20355 genes are subject to the differential expression analysis after QC. Bonferroni correction threshold was used to determine the statistical significance. False discovery rate is also estimated and reported.

Development of 4-Gene Signature

The 13 significant genes from univariate DE analysis are set as candidates for building the signature. The genes are ranked via their fold changes of responder cell lines to non-responder cell lines. Positive genes are defined as those with fold changes higher than 1; whereas negative genes are defined as those with fold changes less than 1. A multivariate logistic regression classifier is then built through a upward model selection procedure to maximize area under the receiver operating characteristic (ROC) curve with 10-fold cross-validation. The mode selection is implemented procedure through R package bestglm. The final selected model is composed of 4 genes. Therefore, each cell line is estimated by a linear combination of their gene-expression values (log transformed RPKM) weighted by their regression coefficients, defined as COMPOUND A signature=$1.43G_{MDM2} + 1.23G_{XPC} + 0.48G_{BBC3} - 0.73G_{CDKN2A}$ Robustness/Reproducability of 4 Gene mRNA Signature Across Various Assayplatforms A robust demonstration of utility of an mRNA signature across various assayplatforms is critical in clinical in development of a biomarker. In the case of this study, the signature is developed with RNAseq quantification of expression measurement, which takes advantage of its sensitivity and the increased dynamic range over microarray technology. As shown in Table 7, the mRNA expression levels of the four genes measured through RNAseq are well correlated with those measured through microarrays. The high discriminatory ability of individual genes and the overall score are preserved through microarray quantification.

TABLE 8

Biosignature genes performance in CELLO and in NP21279

| | CELLO | | | | NO21279 | | | |
|---|---|---|---|---|---|---|---|---|
| | OR (95% CI)[a] | P-value[b] | Correlation Coefficient RNAseq results vs microarray results | P-value | Correlation (efficacy) | P-value | Correlation (change in MDM2) | P-value |
| MDM2 | 4.17 (2.12, 8.19) | 3.41E−05 | 0.73 | 3.50E−19 | 0.14 | 2.32E−01 | 0.22 | 1.49E−01 |
| XPC | 3.42 (1.80, 6.49) | 1.78E−04 | 0.63 | 1.72E−16 | 0.27 | 8.58E−02 | 0.49 | 7.40E−03 |
| BBC3 | 1.62 (0.95, 2.78) | 7.67E−02 | 0.38 | 1.20E−14 | 0.37 | 2.68E−02 | 0.05 | 4.09E−01 |
| CDKN2A | 0.48 (0.29, 0.79) | 4.41E−03 | 0.89 | 2.46E−26 | −0.23 | 1.20E−01 | −0.29 | 7.62E−02 |
| score | 2.53 (1.95, 3.29) | 3.52E−12 | 0.8 | 1.30E−21 | 0.58 | 9.00E−04 | 0.41 | 1.90E−02 |

Example 4

Microarray Gene Expression Analysis Methods

To reduce variation among microarrays, the intensity values for samples in each microarray are resealed by quantile normalization method. Each intensity value is then log 2 transformed.
Validation of the 4-Gene Signature in COMPOUND A Clinical Trials In the NO21279 Phase 1 clinical trial, patients with relapsed/refractory leukemia are treated with ascending doses of COMPOUND A. Specimens from subset of patients treated at the MTD (1500 mg BID×10 days) are evaluated as a part of the current gene expression study. Leukemia samples are collected at baseline, cycle 1 day 2 (C1D2) and cycle 1, day 10 (C1D10) and isolated via MACs separation.

Risk scores are calculated for patients based on their mRNA expression values of the 4 genes at baseline prior to treatment. To ensure a rigorous and an unbiased validation, the compute of the coefficients in the test cohort is not done. However, due to the platform difference and the biological differences between patients and cell lines, in-vitro coefficients for the patient level classifier is not applied. Therefore, the patient's signature scores is simply the sum of expression levels of the signature genes as measured by microarray analysis, multiplied by the observed direction in-vitro, defined as COMPOUND A signature=$G_{MDM2}$+$G_{XPC}$+$G_{BBC3}$|$G_{CDKN2A}$. Note that it is not an optimal combination of the gene expression levels, so the reported association and prediction power of the score is a conservative estimate of the score performance.

Example 5

In Vivo Testing

In the NO21279 Phase 1 clinical trial, patients with relapsed/refractory leukemia are treated with ascending doses of RG7112. Specimens from subset of patients treated at the MTD (1500 mg BID×10 days) are evaluated as a part of the current gene expression study. Leukemia samples are collected at baseline, cycle 1 day 2 (C1D2) and cycle 1, day 10 (C1D10) and isolated via MACs separation.

Patients are composed of 18 men and 10 women with a median age 59 years. Based on tumor specimen assessments, 23 of 28 patients have wild-type TP53, and 5 patients have TP53 mutations (one patient with mutation A to C in intron 7; two patients with mutations CGC to CAC in exon 5; one patient with deletion G 323_3-324_1 in exon 9 farmeshift; one with mutation S240G-S240, AGT to GGT in exon 7). On day 1, median values for the area under the curve of 24 h (AUC0-24 h) for COMPOUND A are 190,315 ng*h/mL (IQR: 119,032-242,857 ng*h/mL) among the 28 studied patients. Clinical responses are evaluated and are divided into 4 categories: Complete Response (CR), Morphologic Leukemia-Free State (MLFS), Hematologic Improvement (HI), and Progressive Disease (PD). Response are evaluated in the 28 patients including 3 CR, 4 MLFS, 6 HI and 15 PD. In addition to assessments of baseline samples, treatment samples are also evaluated (Cycle 1, Day 10). Median MDM2 mRNA expression in biopsies from C1D10 is increased by 2.46 times (IQR: 1.62-4.59) over baseline, demonstrating a pharmacodynamic biomarker response resulting from p53 activation of MDM2 transcription.

Baseline blood cell specimens from 28 evaluable patients dosed at the MTD are evaluated using Affymetrix GeneChip Human Genome U133 Plus 2.0 microarrays. The identified 4-gene signature score is calculated for each of the 28 patients by taking the summation of MDM2, BBC3, XPC, subtracting CDKN2A expression levels at baseline. There is a significant correlation between the signature scores and patients' clinical responses (PD<HI<MLFS<CR) to MDM2 antagonist therapy (Spearman correlation coefficient 0.58, P=6.6×10$^{-4}$). The signature scores also significantly correlate with patients' pharmacodynamic biomarker responses as measured by MDM2 mRNA change from baseline to C1D10 (Spearman correlation coefficient 0.41, P=0.02; FIG. 3). The correlation between the signature scores and patients' clinical responses is further enhanced for the subset of 15 patients with sufficiently high exposures, defined as patients with AUC0-24 h higher than 150,000 ng*h/mL (Spearman correlation coefficient 0.64, P=5.2×10$^{-3}$). This panel was capable of distinguishing CR/MLFS patients from PD/HI patients with an AUC of the ROC curve of 0.82 (FIG. 4A, Table 9), and distinguishing CR/MLFS/HI patients from PD patients with an AUC of 0.83 (FIG. 4A). In contrast, MDM2 mRNA expression as a single biomarker could only distinguish CR/MLFS patients from PD/HI patients with an AUC of 0.51, and distinguish CR/MLFS/HI patients from PD patients with an AUC of 0.61.

TABLE 9

Assessment of the MDM2-antagonist therapy predictive signature

| Patient no. | Response | TP53 Status | AUC$_{0-24}$ (ng*h/mL) | MDM2 mRNA (RT-PCR) fold change over baseline (C1D10) | Patient's signature score at baseline |
|---|---|---|---|---|---|
| 1 | CR | WILD-TYPE | 242,190 | 1.67 | 16.53 |
| 2 | CR | WILD-TYPE | 234,520 | 3.00 | 16.01 |
| 3 | CR | WILD-TYPE | 139,330 | 2.23 | 15.37 |
| 4 | MLFS | WILD-TYPE | 268,300 | 5.67 | 16.18 |
| 5 | MLFS | WILD-TYPE | 247,574 | 5.05 | 15.68 |
| 6 | MLFS | MUTANT | 330,300 | 9.66 | 15.28 |
| 7 | MLFS | WILD-TYPE | 189,500 | 1.79 | 15.23 |
| 8 | HI | WILD-TYPE | 239,490 | 23.00 | 16.49 |
| 9 | HI | WILD-TYPE | 244,860 | 2.01 | 15.93 |
| 10 | HI | WILD-TYPE | 191,130 | 1.72 | 15.75 |
| 11 | HI | WILD-TYPE | 400,900 | 5.07 | 14.92 |
| 12 | HI | WILD-TYPE | 209,420 | 3.20 | 14.66 |
| 13 | HI | WILD-TYPE | 185,630 | 4.35 | 13.95 |
| 14 | PD | WILD-TYPE | 65,080 | 1.27 | 16.36 |
| 15 | PD | MUTANT | NA | NA | 15.47 |
| 16 | PD | WILD-TYPE | 124,790 | 2.51 | 15.46 |
| 17 | PD | WILD-TYPE | 83,480 | 0.96 | 15.27 |
| 18 | PD | WILD-TYPE | NA | NA | 15.14 |
| 19 | PD | WILD-TYPE | 127,530 | 1.69 | 15.00 |
| 20 | PD | WILD-TYPE | NA | NA | 14.99 |
| 21 | PD | WILD-TYPE | 81,720 | 2.26 | 14.86 |
| 22 | PD | WILD-TYPE | 101,760 | 1.52 | 14.84 |
| 23 | PD | MUTANT | 207,580 | 3.88 | 14.83 |
| 24 | PD | WILD-TYPE | NA | 2.65 | 14.68 |
| 25 | PD | WILD-TYPE | 396,800 | 5.11 | 14.07 |
| 26 | PD | WILD-TYPE | 159,120 | 9.46 | 13.90 |
| 27 | PD | MUTANT | 89,740 | 1.00 | 12.93 |
| 28 | PD | MUTANT | 78,630 | 1.59 | 12.41 |
| All patients | 3CR, 4 MLFS, 6 HI, 15 PD | 23 WT, 5 Mutant | 190,325$^a$ (IQR: 119,032-242,857) | Median increase 2.46x (IQR: 1.62-4.59) | Average WT score 15.54 ± 0.16 Average mutant score 14.46 ± 0.63 |

$^a$The median exposure value for the area under the curve of 24 hour (AUC$_{0-24\,h}$) for RG7112 among the 28 studied patients on Day 1.
$^b$AUC$_{0-24\,h}$ less than 150,000 ng*h/mL defined as insufficient exposures Using a cut-off point of the signature score 15 patients are classified into likely-responder group and likely-non-responder group at baseline prior to MDM2 antagonist therapy with 100% sensitivity and 71% specificity. Therefore, the signature panel has significant potential to be used as a companion predictive biomarker of MDM2 antagonist therapy to select a subset of AML patients who are most likely to respond; and avoid exposing the AML patients who are less likely to respond.

To understand the molecular mechanisms underlying the mRNA signature, the mRNA signature score is correlated with mutation status of TP53. Patients with low signature scores are more likely to be TP53 mutants; whereas patients with high signature score are more likely to be TP53 wild type or TP53 mutant with predicted benign mutations (P=6.86×10−2). Among the five p53 mutated patients, four show progressive diseases with average score 14.2±0.8 (one patient with mutation A to C in intron 7; 2 patients with mutations CGC to CAC in exon 5; one patient with deletion G 323_3-324_1 in exon 9 frameshift), while one shows MLFS with mutation S240G-S240, AGT to GGT in exon 7, predicts not direct interact with DNA or with any amino acid residues that interact with DNA by IARC database, and score 15.8. This evidence indicates that the signature score can potentially serve as a surrogate mRNA-level indicator of MDM2-P53 pathway function.

To examine the tissue specificity of the mRNA signature, baseline bone marrow cell specimens are measured from the available subset of 18 patients dosed at the MTD using Affymetrix GeneChip Human Genome U133 Plus 2.0 microarrays. The blood-signature score and bone-marrow-signature score are significantly correlated with Spearman correlation coefficient 0.50 (P=0.016). The bone-marrow-signature scores were significantly correlated with patients' clinical responses and pharmacodynamic biomarker responses (MDM2 expression change from cycle 1 day 1 to cycle 1 day 10) to MDM2 antagonist therapy with Spearman correlation coefficients 0.46 (P=0.052) and 0.42 (P=0.069) respectively.

To study the pharmacodynamics properties of the mRNA signature, blood cell specimens are measured from most of the 28 patients on C1D10 and derived the signature on C1D10. Median MDM2, XPC and BBC3 mRNA expression in samples from C1D10 is 2.37 times (IQR: 1.71-5.00), 1.69 times (IQR: 1.27-1.88), 1.45 times (IQR: 1.13-1.99) over baseline, demonstrating up-regulation of respective genes stimulated by MDM2 antagonist therapy for the positively correlated genes in the signature. On the other hand, median CDKN2A mRNA expression in biopsies from C1D10 is decreased by 0.26 times (IQR: 0.09-0.38) over baseline, demonstrating a down-regulation stimulated by MDM2 antagonist therapy for the negatively correlated gene in the signature. Therefore, the overall signature score in biopsies from C1D10 is 3.05 times (IQR: 1.88-4.23) over baseline, demonstrating an up-regulation of the overall score stimulated by MDM2 antagonist therapy. In summary, the signature scores are correlated with patients' clinical responses consistently when measured at baseline (correlation coefficient 0.58, P=9×10−4), and during the treatment regimen: C1D2 (correlation coefficient 0.40, P=2.69×10−2), and C1D10 (correlation coefficient 0.65, P=3.5×10−4). The signature score measurements are also correlated with patients' pharmacodynamic biomarker responses (MDM2 expression change) consistently when measured at baseline (correlation coefficient 0.41, P=1.92×10−2), C1D2 (correlation coefficient 0.64, P=1.07×10−3), and C1D10 (correlation coefficient 0.64, P=3.3×10−4). Median signature score on C1D2 is 1.11 times (IQR: 1.05-1.16), 1.08 times (IQR: 1.04-1.10), 1.17 times (IQR: 1.14-1.19), and 1.15 times (IQR: 1.13-1.15) over baseline for PD, HI, MLFS and CR patients respectively. Median score on C1D10 is 1.14 times (IQR: 1.08-1.21), 1.25 times (IQR: 1.23-1.30), 1.26 times (IQR: 1.23-1.31), and 1.23 times (IQR: 1.22-1.24) over baseline for PD, HI, MLFS and CR patients respectively. This evidence indicates that the mRNA signature score is both a predictive biomarker and a pharmacodynamics biomarker of MDM2 antagonist therapyactivity. The baseline mRNA signature score is thus predictive of patients' responses to MDM2 inhibitor, and MDM2 antagonist therapy stimulates patients by various extents during the treatment cycle that is indicative of the patients' clinical responses (FIG. 3).

Example 6

Figure 1:
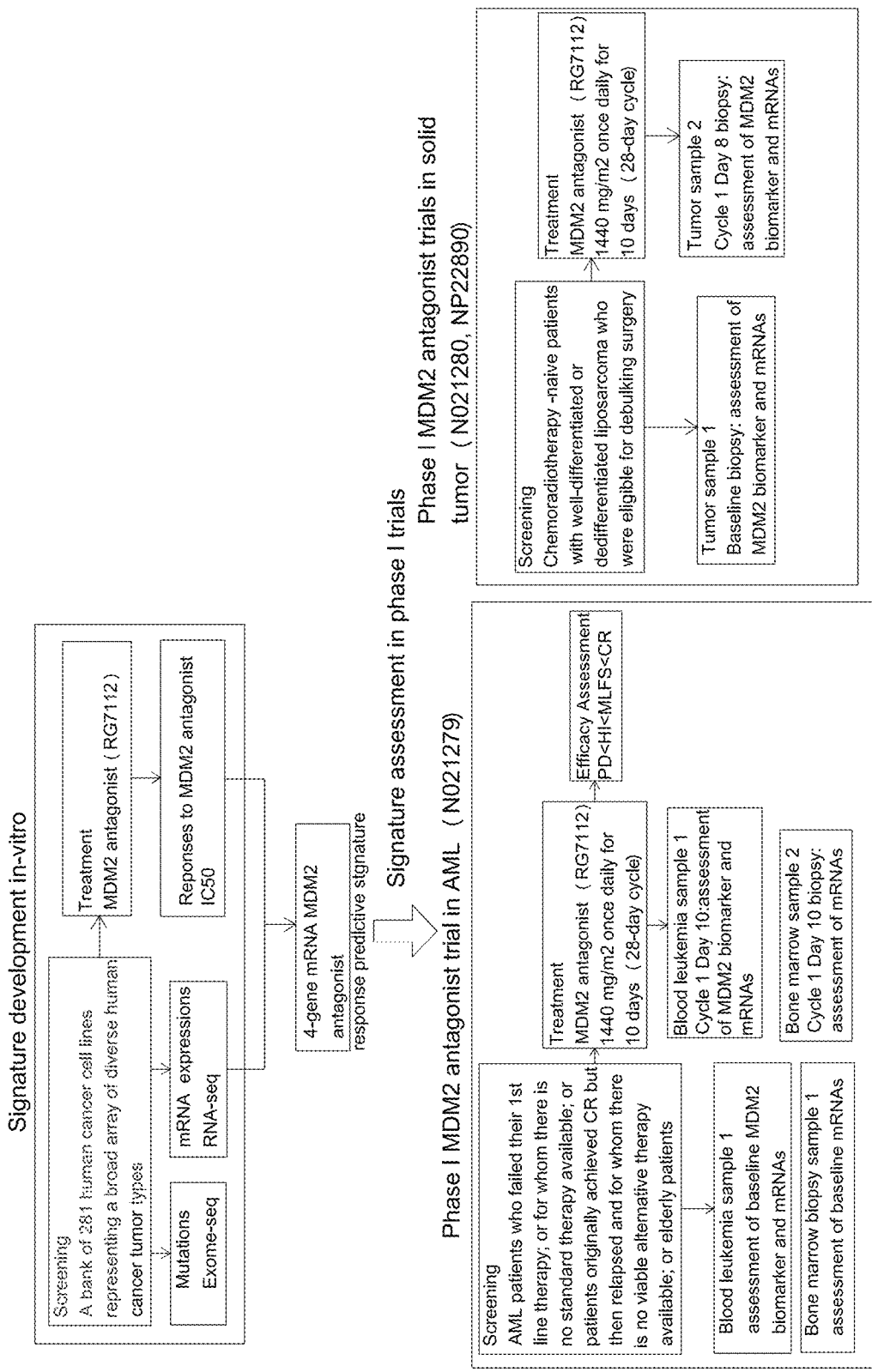
FIG. 1: This outline provides the sequence of work that forms the invention.

Assessment of MDM2 Antagonist Therapy Predictive Signature in Phase I Solid Tumors Trials The predictive mRNA signature is also evaluated in two solid tumor trials (FIG. 1). In trial NP21280 30 patients with pretreatment and C1D5 tumor biopsy samples are evaluated; and in NP22890 20 patients with pretreatment and C1D8 tumor biopsy samples are evaluated (Table 6). In both clinical trials, a biomarker package that enabled assessment of p53 pathway activation is assessed (p53 IHC, p21 IHC, MDM2 mRNA, and Ki67), MDM2 inhibition activates the P53 pathway and decreases cell proliferation. As previously reported, P53 and P21 concentrations, and MDM2 mRNA expression all significantly increase at C1D8 from baseline, and Ki-67-positive tumor cells are decreased from baseline in NP22890. These changes in biomarker responses are not significantly correlated with drug exposure, except for MIC-1 change12. In NP21280, P53 and P21 concentrations, and MDM2 mRNA expressions, all significantly increase at C1D10 from baseline (p=2.88×10−3, 2.32×10−3, 1.03×10−5, respectively); and Ki-67-positive tumor cells are decreased from baseline (p=2.62×10−2). These changes in biomarker responses are also significantly correlated with drug exposure (p=4.77×10−3 for P53 change, p=5.30×10−2 for P21 change, and p=2.5×10−3 for MDM2 change), except for the number of Ki-67-positive tumor cells.

The signature scores are similarly derived for patients at baseline and at C1D5 (NO21280) and C1D8 (NP22890). The mRNA signature scores show heterogeneous magnitudes of the correlations with the COMPOUND A pharmaco-kinetics and pharmacodynamic marker panels and between the two trials. In NP21280, the baseline score significantly correlates with patients' MDM2 mRNA expression change with correlation coefficient 0.41 (p=2.82×10−2), but no significant correlation between the signature score and P21 or the number of Ki-67-positive tumor cells is observed. In NP22890, only a suggestion of a positive correlation between the signature score and MDM2 change and P21 change are observed (Table 10). No assessment of clinical outcomes is feasible for the solid tumor trial specimens.

TABLE 10

Correlation between score and biomarker response in NO21280 and NP22890

| | NO21280 | | NP22890 | |
|---|---|---|---|---|
| | Correlation coefficient | P-value | Correlation coefficient | P-value |
| Ki-67 Change | −0.20 | 2.25E−01 | 0.35 | 8.82E−01 |
| P53 Change | 0.06 | 4.15E−01 | −0.06 | 5.76E−01 |
| P21 Change | 0.17 | 2.85E−01 | 0.16 | 3.01E−01 |
| MDM2 Change | 0.41 | 2.82E−02 | 0.25 | 1.85E−01 |

REFERENCES CITED

Patent Literature

WO 2007/063013
WO2011/098398
U.S. Pat. No. 8,354,444 B2

NON-PATENT LITERATURE

1. Vogelstein B, Lane D, Levine A J. Surfing the p53 network. Nature. 2000; 408(6810): 307-10.
2. Hainaut P, Hollstein M. p53 and human cancer: the first ten thousand mutations. Adv Cancer Res. 2000; 77: 81-137.
3. Harris S L, Levine A J. The p53 pathway: positive and negative feedback loops. Oncogene. 2005; 24(17): 2899-908.
4. Oren M. Decision making by p53: life, death and cancer. Cell Death Differ. 2003; 10(4): 431-42.
5. Shangary S, Wang S. Small-molecule inhibitors of the MDM2-p53 protein-protein interaction to reactivate p53 function: a novel approach for cancer therapy. Annu Rev Pharmacol Toxicol. 2009; 49: 223-41.
6. Manfredi J J. The Mdm2-p53 relationship evolves: Mdm2 swings both ways as an oncogene and a tumor suppressor. Genes Dev. 2010; 24(15): 1580-9.
7. Vassilev L T. MDM2 inhibitors for cancer therapy. Trends Mol Med. 2007; 13(1): 23-31.
8. Kojima K, Konopleva M, Samudio I J, Shikami M, Cabreira-Hansen M, McQueen T, et al. MDM2 antagonists induce p53-dependent apoptosis in AML: implications for leukemia therapy. Blood. 2005; 106(9): 3150-9.
9. Vassilev L T, Vu B T, Graves B, Carvajal D, Podlaski F, Filipovic Z, et al. In vivo activation of the p53 pathway by small-molecule antagonists of MDM2. Science. 2004; 303(5659): 844-8.
10. Tovar C, Graves B, Packman K, Filipovic Z, Xia B H, Tardell C, et al. MDM2 Small-Molecule Antagonist RG7112 Activates p53 Signaling and Regresses Human Tumors in Preclinical Cancer Models. Cancer Res. 2013; 73(8): 2587-97.
11. Ray-Coquard I, Blay J Y, Italiano A, Le Cesne A, Penel N, Zhi J, et al. Effect of the MDM2 antagonist RG7112 on the P53 pathway in patients with MDM2-amplified, well-differentiated or dedifferentiated liposarcoma: an exploratory proof-of-mechanism study. Lancet Oncol. 2012; 13(11): 1133-40.
12. Thompson T, Andreeff M, Studzinski G P, Vassilev L T. 1,25-dihydroxyvitamin D3 enhances the apoptotic activity of MDM2 antagonist nutlin-3a in acute myeloid leukemia cells expressing wild-type p53. Mol Cancer Ther. 2010; 9(5): 1158-68.

13. Genomic and epigenomic landscapes of adult de novo acute myeloid leukemia. N Engl J Med. 2013; 368(22): 2059-74.
14. Chiaretti S, Tavolaro S, Marinelli M, Messina M, Del Giudice I, Mauro F R, et al. Evaluation of TP53 mutations with the AmpliChip p53 research test in chronic lymphocytic leukemia: correlation with clinical outcome and gene expression profiling. Genes Chromosomes Cancer. 2011; 50(4): 263-74.
15. Bolstad B M, Irizarry R A, Astrand M, Speed T P. A comparison of normalization methods for high density oligonucleotide array data based on variance and bias. Bioinformatics. 2003; 19(2): 185-93.
16. van Bokhoven A, Varella-Garcia M, Korch C, Johannes W U, Smith E E, Miller H L, et al. Molecular characterization of human prostate carcinoma cell lines. Prostate. 2003; 57(3): 205-25.
17. Petitjean A, Mathe E, Kato S, Ishioka C, Tavtigian S V, Hainaut P, et al. Impact of mutant p53 functional properties on TP53 mutation patterns and tumor phenotype: lessons from recent developments in the IARC TP53 database. Hum Mutat. 2007; 28(6): 622-9.
18. Ding Q, Zhang Z, Liu J J, Jiang N, Zhang J, Ross T M, et al. Discovery of RG7388, a Potent and Selective p53-MDM2 Inhibitor in Clinical Development. J Med Chem. 2013.
19. Barretina J, Caponigro G, Stransky N, Venkatesan K, Margolin A A, Kim S, et al. The Cancer Cell Line Encyclopedia enables predictive modelling of anticancer drug sensitivity. Nature. 2012; 483(7391): 603-7.
20. Garnett M J, Edelman E J, Heidom S J, Greenman C D, Dastur A, Lau K W, et al. Systematic identification of genomic markers of drug sensitivity in cancer cells. Nature. 2012; 483(7391): 570-5.
21. Higgins B, Tovar C, Glenn K, et al. Antitumor activity of the MDM2 antagonist RG7388. 2013; AACR-NCI-EORTC International Conference on Molecular Targets and Cancer Therapeutics: Abstr B55
22. Hercus, C. Novoalign short read alignment package. 2008; http://www.novocraft.com
23. Li H, Handsaker B, Wysoker A, et al. The sequence alignment/map format and SAMtools. *Bioinformatics* 2009; 25:2078-2079.
24. Picard. http://picard.sourceforge.net, accessed December 2011
25. DePristo M A, Banks E, Poplin R, et al. A framework for variation discovery and genotyping using next-generation DNA sequencing data. *Nat Genet* 2011; 43:491-498.
26. Albers C A, Lunter G, Macarthur D G, et al. Dindel: Accurate indel calls from short-read data. *Genome research* 2011; 21: 961-973.
27. Cingolani P, Platts A, Wang le L, et al. A program for annotating and predicting the effects of single nucleotide polymorphisms, SnpEff: SNPs in the genome of *Drosophila melanogaster* strain w1118; iso-2; iso-3. *Fly (Austin)* 2012; 6: 80-92.SIFT
28. Adzhubei I, Schmidt S, Peshkin L, Ramensky V E, Gerasimova A, Bork P. et al. A method and server for predicting damaging missense mutations. *Nat Methods* 2010; 7:248-249.
29. Ramensky V, Bork P, Sunyaev S. Human non-synonymous SNPs: server and survey. *Nucleic Acids Res* 2002; 30: 3894-3900.
30. FASTQC. (http://www.bioinfonnatics.babraham.ac.uk/projects/fastqc/), accessed June 2012
31. Bolstad B M, Irizarry R A, Astrand M, et al. A comparison of normalization methods for high density oligonucleotide array data based on variance and bias. *Bioinformatics* 2003; 19: 185-93.
32. Ansel et al., Pharmaceutical Dosage Forms and Drug Delivery Systems (6th Ed. 1995) at pp. 196 and 1456-1457.

What is claimed:

1. A method to predict responsiveness of a cancer patient to chemotherapy treatment, comprising the steps of:
   a) obtaining a sample from said patient being treated with a compound of formula I, II or III:

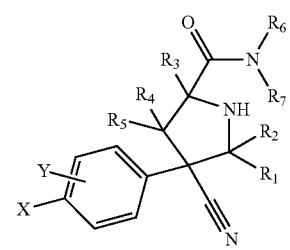

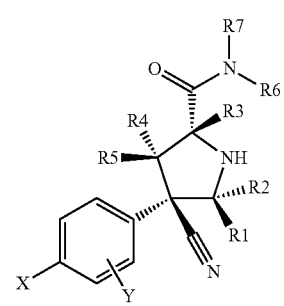

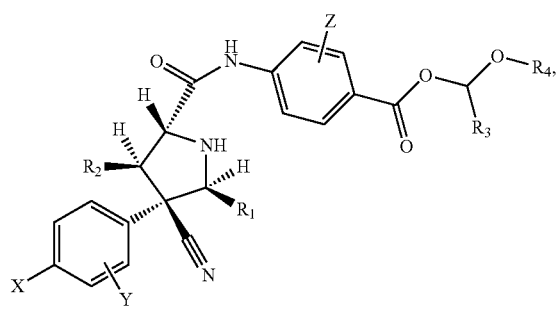

or a pharmaceutically acceptable salt or ester individually thereof, or a combination thereof;
   b) measuring the response to said treatment by measuring at least a MDM2 biomarker in vitro from said sample;
   c) comparing values obtained from step b) to a standard set of values; and
   d) adjusting the chemotherapy administered to the patient accordingly.

2. The method according to claim 1, wherein the compound is:

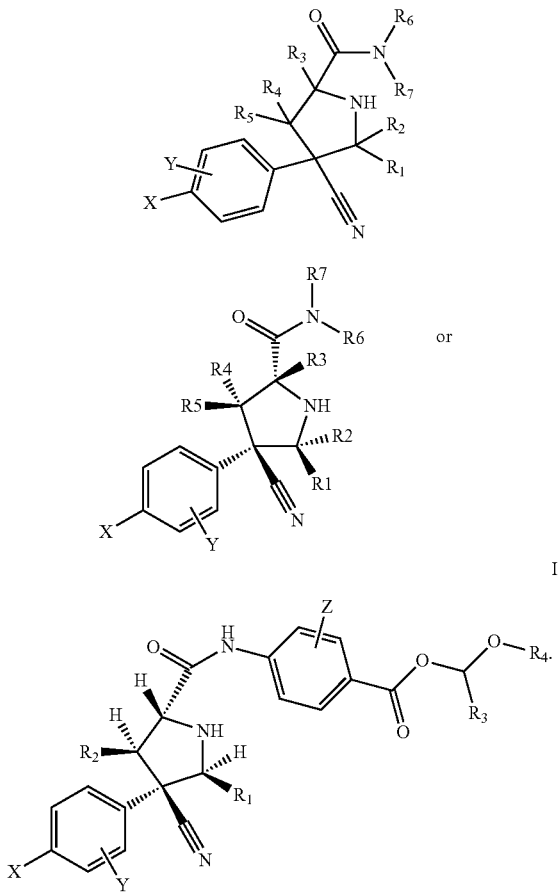

3. The method according to claim 1, wherein the compound is 4-{[2R,3 S,4R,5 S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid; or 4-{[(2R,3 S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2000); or a pharmaceutically acceptable salt or ester individually thereof, or a combination thereof.

4. The method according to claim 1, wherein said biomarker is at least the MDM2 gene.

5. The method according to claim 4, wherein said biomarker is as four-gene MDM2 biomarker panel is used.

6. The method according to claim 5, wherein said biomarker is at least the MDM2 gene, two upregulated genes and one down regulated gene.

7. The method according to claim 5, wherein said four gene panel comprises: MDM2, XPC, BBC3 and CDKN2A.

8. The method according to claim 1, wherein the cancer is selected from the group consisting of breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma and sarcomas.

9. The method according to claim 8, wherein the cancer is acute myeloid leukemia (AML).

10. The method according to claim 1, wherein a higher level of MDM2 in the sample from the patient relative to a standard value or set of standard values predicts sensitivity to a compound of formula I, II or III, or a pharmaceutically acceptable salt or ester individually thereof, or a combination thereof.

11. The method according to claim 10, wherein higher MDM2 levels in a sample or samples
   i) relative to a standard value or set of standard values from a patient with the same cancer; or
   ii) taken after treatment initiation and compared to a sample or samples taken from the same patient before treatment initiation; or
   iii) relative to a standard value or set of standard values from normal cells or tissues;
   are predictive of sensitivity to a compound of formula I, II or III, or a pharmaceutically acceptable salt or ester individually thereof, or a combination thereof.

12. A method for predicting the response of a patient with cancer to a compound of general formula I, II or III, or a pharmaceutically acceptable salt or ester individually thereof, or a combination thereof, said method comprising the steps of:
   a) measuring a level of MDM2 in a sample pre-obtained from the patient to obtain a value or values representing this level;
   b) comparing the value or values from step a) to a standard value or set of standard values; and
   c) adjusting the chemotherapy administered to the patient.

13. The method according to claim 9, wherein the response which is predicted is sensitivity to a compound of formula I, II or III, or a pharmaceutically acceptable salt or ester individually thereof, or a combination thereof.

14. A method of treating cancer, in a patient in need thereof, said method comprising; measuring a level of MDM2 in a sample from the patient to obtain a baseline value or values, and treating the patient with a compound of formula I, II or III, or a pharmaceutically acceptable salt or ester individually thereof, or a combination thereof.

15. A method for treating cancer, in a patient in need thereof according to claim 14, wherein said method treats the patient with the compound 4-{[2R,3S,4R,5S)-4-(4-Cholor-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid; or 4-{[(2R,3 S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2000); or a pharmaceutically acceptable salt or ester individually thereof, or a combination thereof.

16. A kit for predicting the response to a compound of formula I, II or III, or a pharmaceutically acceptable salt or ester individually thereof, or a combination thereof, comprising;
   a) reagents for measuring a level of MDM2 in a sample; and
   b) a comparator module.

* * * * *

UNITED STATES PATENT AND TRADEMARK OFFICE
CERTIFICATE OF CORRECTION

| | |
|---|---|
| PATENT NO. | : 9,657,351 B2 |
| APPLICATION NO. | : 14/560519 |
| DATED | : May 23, 2017 |
| INVENTOR(S) | : Hua Zhong et al. |

Page 1 of 1

It is certified that error appears in the above-identified patent and that said Letters Patent is hereby corrected as shown below:

On the Title Page

(73) Assignee should read as follows:
--Hoffmann-La Roche Inc., Nutley, NJ (US)--

Signed and Sealed this
Eleventh Day of July, 2017

Joseph Matal
*Performing the Functions and Duties of the
Under Secretary of Commerce for Intellectual Property and
Director of the United States Patent and Trademark Office*